US012788733B2

(12) United States Patent
Rizvi et al.

(10) Patent No.: US 12,788,733 B2
(45) Date of Patent: Nov. 10, 2026

(54) ANTI-VIRAL THERAPEUTIC AGENTS AND USES THEREOF

(71) Applicant: Cila Therapeutics Inc., Jamaica Plain, MA (US)

(72) Inventors: Safia K. Rizvi, Jamaica Plain, MA (US); Larry Lands, Hampstead (CA)

(73) Assignee: Cila Therapeutics Inc., Jamaica Plain (MA)

( * ) Notice: Subject to any disclaimer, the term of this patent is extended or adjusted under 35 U.S.C. 154(b) by 16 days.

(21) Appl. No.: 18/737,662

(22) Filed: Jun. 7, 2024

(65) Prior Publication Data

US 2024/0307333 A1 Sep. 19, 2024

Related U.S. Application Data

(63) Continuation of application No. PCT/US2022/081081, filed on Dec. 7, 2022.

(60) Provisional application No. 63/286,769, filed on Dec. 7, 2021.

(51) Int. Cl.

| | |
|---|---|
| ***A61K 31/185*** | (2006.01) |
| ***A61K 9/16*** | (2006.01) |
| ***A61K 31/145*** | (2006.01) |
| ***A61K 45/06*** | (2006.01) |

(52) U.S. Cl.

CPC .......... *A61K 31/185* (2013.01); *A61K 9/1617* (2013.01); *A61K 31/145* (2013.01); *A61K 45/06* (2013.01)

(58) Field of Classification Search

None

See application file for complete search history.

(56) References Cited

U.S. PATENT DOCUMENTS

| | | | | |
|---|---|---|---|---|
| 2006/0189688 | A1 | 8/2006 | Piazza et al. | |
| 2007/0135525 | A1 | 6/2007 | Liang et al. | |
| 2009/0155349 | A1* | 6/2009 | Heller | A61P 25/16 514/459 |
| 2012/0129946 | A1* | 5/2012 | Thoene | A61P 31/16 514/665 |
| 2019/0070132 | A1* | 3/2019 | Stanton, Jr. | A61K 9/5084 |
| 2019/0175501 | A1* | 6/2019 | O'Neil | A61K 9/0075 |

FOREIGN PATENT DOCUMENTS

| | | | |
|---|---|---|---|
| WO | 2021194890 | A1 | 9/2021 |
| WO | 2021231421 | A1 | 11/2021 |
| WO | 2021231570 | A1 | 11/2021 |
| WO | 2023107996 | A1 | 6/2023 |

OTHER PUBLICATIONS

Su et al. (Drug Deliv. Jun. 29, 2021;28(1):1397-1418).*

International Search Report; PCT/US2022/081081; Date: May 8, 2023, By: Authorized Officer Kari Rodriquez.

* cited by examiner

*Primary Examiner* — Bong-Sook Baek

(74) *Attorney, Agent, or Firm* — Wiggin and Dana LLP

(57) ABSTRACT

The present invention is related to compositions and methods for the reduction of risk and treatment of a viral infection in a subject, wherein the method includes administering to the subject a composition including sodium 2-mercaptoethane sulfonate or 2-mercaptoethylamine particles.

13 Claims, 6 Drawing Sheets

Specification includes a Sequence Listing.

A) Alpha (B.1.1.7) RBD region

| | | |
|---|---|---|
| SARS-COV-2 481 | NGVEG FNCYF PLQSY GFQPT NGVGY QPYRV VVLSF ELLHA PATVC GPKKS TNLVK NKCVN | 540 |
| Alpha Variant | NGVEG FNCYF PLQSY GFQPT YGVGY QPYRV VVLSF ELLHA PATVC GPKKS TNLVK NKCVN | |
| SARS-COV-2 541 | FNFNG LTGTG VLTES NKKFL PFQQF GRDIA DTTDA VRDPQ TLEIL DIPTC SFGGV SVITP | 600 |
| Alpha Variant | FNFNG LTGTG VLTES NKKFL PFQQF GRDID DTTDA VRDPQ TLEIL DIPTC SFGGV SVITP | |
| SARS-COV-2 661 | ECDIP IGAGI CASYQ TQTNS PRRAR SVASQ SIIAY TMSLG AENSV AYSNN SIAIP TNFTI | 720 |
| Alpha Variant | ECDIP IGAGI CASYQ TQTNS HRRAR SVASQ SIIAY TMSLG AENSV AYSNN SIAIP INFTI | |
| SARS-COV-2 961 | TLVKQ LSSNF GAISS VLNDI LSRLD KVEAE VQIDR LITGR LQSLQ TYVTQ QLIRA AEIRA | 1020 |
| Alpha Variant | TLVKQ LSSNF GAISS VLNDI LARLD KVEAE VQIDR LITGR LQSLQ TYVTQ QLIRA AEIRA | |
| SARS-COV-2 1081 | ICHDG KAHFP REGVF VSNGT HWFVT QRNFY EPQII TTDNT FVSGN CDVVI GIVNN TVYDP | 1140 |
| Alpha Variant | ICHDG KAHFP REGVF VSNGT HWFVT QRNFY EPQII TTHNT FVSGN CDVVI GIVNN TVYDP | |

FIG. 1A

B) Beta (B.1.351)

| | | |
|---|---|---|
| SARS-COV-2 61 | NVTWF HAIHV SGTNG TKRFD NPVLP FNDGV YFAST EKSNI IRGWI FGTTL DSKTQ SLLIV | 120 |
| Beta Variant | NVTWF HAIHV SGTNG TKRF**A** NPVLP FNDGV YFAST EKSNI IRGWI FGTTL DSKTQ SLLIV | |
| SARS-COV-2 181 | GKQGN FKNLR EFVFK NIDGY FKIYS KHTPI NLVRD LPQGF SALEP LVDLP IGINI TRFQT | 240 |
| Beta Variant | GKQGN FKNLR EFVFK NIDGY FKIYS KHTPI NLVR**G** LPQGF SALEP LVDLP IGINI TRFQT | |

RBD region

| | | |
|---|---|---|
| SARS-COV-2 361 | CVADY SVLYN SASFS TFKCY GVSPT KLNDL CFTNV YADSF VIRGD EVRQI APGQT GKIAD | 420 |
| Beta Variant | CVADY SVLYN SASFS TFKCY GVSPT KLNDL CFTNV YADSF VIRGD EVRQI APGQT G**N**IAD | |

RBD region

| | | |
|---|---|---|
| SARS-COV-2 481 | NGVEG FNCYF PLQSY GFQPT NGVGY QPYRV VVLSF ELLHA PATVC GPKKS TNLVK NKCVN | 540 |
| Beta Variant | NGV**K**G FNCYF PLQSY GFQPT **Y**GVGY QPYRV VVLSF ELLHA PATVC GPKKS TNLVK NKCVN | |

| | | |
|---|---|---|
| SARS-COV-2 661 | ECDIP IGAGI CASYQ TQTNS PRRAR SVASQ SIIAY TMSLG AENSV AYSNN SIAIP TNFTI | 720 |
| Beta Variant | ECDIP IGAGI CASYQ TQTNS PRRAR SVASQ SIIAY TMSLG **V**ENSV AYSNN SIAIP TNFTI | |

FIG. 1B

C) Gamma (P.1)

| | | |
|---|---|---|
| SARS-COV-2 1 | MFVFL VLLPL VSSQS VNLTT RTQLP PAYTN SFTRG VYYPD KVFRS SVLHS TQDLF LPFFS | 60 |
| Gamma Variant | MFVFL VLLPL VSSQS VNFTN RTQLP SAYTN SFTRG VYYPD KVFRS SVLHS TQDLF LPFFS | |
| SARS-COV-2 121 | NNATN VVIKV CEFQF CNDPF LGVYY HKNNK SWMES EFRVY SSANN CTFEY VSQPF LMDLE | 180 |
| Gamma Variant | NNATN VVIKV CEFQF CNYPF LGVYY HKNNK SWMES EFRVY SSANN CTFEY VSQPF LMDLE | |
| SARS-COV-2 181 | GKQGN FKNLR EFVFK NIDGY FKIYS KHTPI NLVRD LPQGF SALEP LVDLP IGINI TRFQT | 240 |
| Gamma Variant | GKQGN FKNLR EFVFK NIDGY FKIYS KHTPI NLVRG LPQGF SALEP LVDLP IGINI TRFQT | |
| | **RBD region** | |
| SARS-COV-2 361 | CVADY SVLYN SASFS TFKCY GVSPT KLNDL CFTNV YADSF VIRGD EVRQI APGQT GKIAD | 420 |
| Gamma Variant | CVADY SVLYN SASFS TFKCY GVSPT KLNDL CFTNV YADSF VIRGD EVRQI APGQT GTIAD | |
| | **RBD region** | |
| SARS-COV-2 481 | NGVEG FNCYF PLQSY GFQPT NGVGY QPYRV VVLSF ELLHA PATVC GPKKS TNLVK NKCVN | 540 |
| Gamma Variant | NGVKG FNCYF PLQSY GFQPT YGVGY QPYRV VVLSF ELLHA PATVC GPKKS TNLVK NKCVN | |
| SARS-COV-2 601 | GTNTS NQVAV LYQDV NCTEV PVAIH ADQLT PTWRV YSTGS NVFQT RAGCL IGAEH VNNSY | 660 |
| Gamma Variant | GTNTS NQVAV LYQDV NCTEV PVAIH ADQLT PTWRV YSTGS NVFQT RAGCL IGAEY VNNSY | |
| SARS-COV-2 1021 | SANLA ATKMS ECVLG QSKRV DFCGK GYHLM SFPQS APHGV VFLHV TYVPA QEKNF TTAPA | 1080 |
| Gamma Variant | SANLA AIKMS ECVLG QSKRV DFCGK GYHLM SFPQS APHGV VFLHV TYVPA QEKNF TTAPA | |

FIG. 1C

D) Delta (B.1.617.2)

| | | |
|---|---|---|
| SARS-COV-2 1 | MFVFL VLLPL VSSQS VNLTT RTQLP PAYTN SFTRG VYYPD KVFRS SVLHS TQDLF LPFFS | 60 |
| Delta Variant | MFVFL VLLPL VSSQS VN**FRN** RTQLP **S**AYTN SFTRG VYYPD KVFRS SVLHS TQDLF LPFFS | |

RBD region

| | | |
|---|---|---|
| SARS-COV-2 421 | YNYKL PDDFT GCVIA WNSNN LDSKV GGNYN YLYRL FRSKN LKPFE RDIST EIYQA GSTPC | 480 |
| Delta Variant | YNYKL PDDFT GCVIA WNSNN LDSKV GGNYN Y**R**YRL FRSKN LKPFE RDIST EIYQA GS**K**PC | |

| | | |
|---|---|---|
| SARS-COV-2 661 | ECDIP IGAGI CASYQ TQTNS PRRAR SVASQ SIIAY TMSLG AENSV AYSNN SIAIP TNFTI | 720 |
| Delta Variant | ECDIP IGAGI CASYQ TQTNS **R**RRAR SVASQ SIIAY TMSLG AENSV AYSNN SIAIP TNFTI | |
| SARS-COV-2 901 | QMAYR FNGIG VTQNV LYENQ KLIAN QFNSA IGKIQ DSLSS TASAL GKLQD VVNQN AQALN | 960 |
| Delta Variant | QMAYR FNGIG VTQNV LYENQ KLIAN QFNSA IGKIQ DSLSS TASAL GKLQ**N** VVNQN AQALN | |

FIG. 1D

ANTI-VIRAL THERAPEUTIC AGENTS AND USES THEREOF

CROSS-REFERENCE TO RELATED APPLICATIONS

This application is a continuation of International Patent Application No. PCT/US2022/081081, filed on Dec. 7, 2022, and entitled "ANTI-VIRAL THERAPEUTIC AGENTS AND USES THEREOF", which claims the benefit of priority of U.S. Provisional Application Ser. No. 63/286,769, filed on Dec. 7, 2021, and entitled "ANTI-VIRAL THERAPEUTIC AGENTS AND USES THEREOF". The entirety of International Patent Application No. PCT/US2022/081081 and U.S. Provisional Application Ser. No. 63/286,769 are incorporated herein by reference.

FIELD OF THE INVENTION

The present invention generally relates to the field of therapeutics. In particular, the present invention is directed to compositions and methods for the reduction of risk and treatment of a viral infection in a subject.

REFERENCE TO SEQUENCE LISTING

This specification includes a sequence listing submitted herewith, which includes the file entitled 1579-004USU1.xml having the following size: 34,257 bytes which was created Jun. 7, 2024, the contents of which are incorporated by reference herein.

BACKGROUND

Viruses represent a dire threat to human health. Viruses infect host cells, forcing the host cell to replicate the original virus. Viruses remain difficult to treat due to their ability to mutate, resulting in reduced efficacy of treatments designed specifically to address the original variant. Reliable methods remain elusive for prevention and treatment of viral infections with a mechanism of action applicable for new variants.

SUMMARY OF THE DISCLOSURE

In an aspect, the present invention may be related to compositions and methods for the reduction of risk and the treatment of viral infections. In one embodiment, the present invention may provide methods of reducing the risk of viral infection in a subject at risk of a viral infection or treating a viral infection in an infected subject, the method including the step of administering to the subject a composition containing sodium 2-mercaptoethane sulfonate or 2-mercaptoethylamine particles. In one embodiment, the subject may be administered a composition containing sodium 2-mercaptoethane sulfonate particles. In another embodiment, the subject may be administered a composition containing 2-mercaptoethylamine particles. In some embodiments, the viral infection may include coronavirus. In some embodiments, the viral infection may include severe acute respiratory syndrome coronavirus (SARS-CoV). In some embodiments, the viral infection may include severe acute respiratory syndrome coronavirus 2 (SARS-COV-2). In some embodiments, the viral infection may include a SARS-COV-2 variant. In some embodiments, the variant may include Delta (B.1.617.2, SEQ ID NO: 32-35), Alpha (B.1.1.7, SEQ ID NO: 15-19), Gamma (P.1, SEQ ID NO: 25-31), Beta (B.1.351, SEQ ID NO: 20-24), or Omicron (B.1.1.529). In some embodiments, the viral infection may include a rhinovirus. In some embodiments, the viral infection may include respiratory syncytial virus (RSV). In some embodiments, the viral infection may include an infection of an avian influenza virus; influenza A, B, or C virus; an adenovirus; a herpesvirus; a human papillomavirus, such as HPV; a parvovirus; a reovirus: a picornavirus; a flavivirus; a togavirus; an orthomyxovirus; a bunyavirus; a rhabdovirus; a paramyxovirus; herpes simplex virus; varicella zoster virus; parvovirus B19; canine parvovirus; an orbivirus; a rotavirus (e.g., Rotavirus A; Rotavirus B; or Rotavirus C); an aquarcovirus; a coltivirus; an enterovirus (e.g., enterovirus 68, 70); a hepatovirus; a torovirus; a petsivirus; an alphavirus; a rubivirus; Thogoto virus; Hantavirus; Nairovirus; a phlebovirus; Punta toro phlebovirus; an adeno-associated virus; Aichi virus; Australian bat lyssavirus; BK polyomavirus; Banna virus; Barmah forest virus; Bunyamwera virus; Bunyavirus La Crosse; Bunyavirus snowshoe hare; Cercopithecine herpesvirus; Chandipura virus; Chikungunya virus; Cosavirus A; Cowpox virus; Coxsackievirus; Crimean-Congo hemorrhagic fever virus; Dengue virus; Dhori virus; Dugbe virus; Duvenhage virus; Eastern equine encephalitis virus; Ebolavirus; Echovirus; Encephalomyocarditis virus; Epstein-Barr virus; European bat lyssavirus; Hantaan virus; Hendra virus; Hepatitis A virus; Hepatitis B virus; Hepatitis C virus; Hepatitis E virus; delta virus; Horsepox virus; astrovirus; cytomegalovirus; herpesvirus 1; herpesvirus 2; herpesvirus 6; herpesvirus 7; herpesvirus 8; immunodeficiency virus; papillomavirus 1; papillomavirus 2; papillomavirus 16,18; parainfluenza; spumaretrovirus; T-lymphotropic virus; Isfahan virus; JC polyomavirus; Japanese encephalitis virus; Junin arenavirus; KI Polyomavirus; Kunjin virus; Lagos bat virus; Lake Victoria marburgvirus; Langat virus; Lassa virus; Lordsdale virus; Louping ill virus; Lymphocytic choriomeningitis virus; Machupo virus; Mayaro virus; MERS coronavirus; Measles virus; Mengo encephalomyocarditis virus; Merkel cell polyomavirus; Mokola virus; Molluscum contagiosum virus; Monkeypox virus; Mumps virus; Murray valley encephalitis virus; New York virus; Nipah virus; Norwalk virus; O'nyong-nyong virus; Orf virus; Oropouche virus; Pichinde virus; Poliovirus; Puumala virus; Rabies virus; Rift valley fever virus; Rosavirus A; Ross river virus; Rubella virus; Sagiyama virus; Salivirus A; Sandfly fever sicilian virus; Sapporo virus; SARS coronavirus 2; Semliki forest virus; Seoul virus; Simian foamy virus; Simian virus 5; Sindbis virus; Southampton virus; St. louis encephalitis virus; Tick-borne powassan virus; Torque teno virus; Toscana virus; Uukuniemi virus; Vaccinia virus; Variola virus; Venezuelan equine encephalitis virus; Vesicular stomatitis virus; Western equine encephalitis virus; WU polyomavirus; West Nile virus; Yaba monkey tumor virus; Yaba-like disease virus; Yellow fever virus; Zika virus; an ephemerovirus; or a vesiculovirus. In some embodiments, the subject may be diagnosed with a medical condition. In some embodiments, the medical condition may include lung disease, sinus disease, airway disease, car disease, heart disease, high blood pressure, diabetes, kidney disease, liver disease, gastrointestinal disease, central nervous system (CNS) disease, dementia, Alzheimer's disease, stroke, an immunocompromised state, cancer, or obesity. In some embodiments, lung, sinus, airway, or car disease may include primary ciliary dyskinesia, cystic fibrosis, sinusitis, rhinosinusitis, bronchiolitis obliterans, plastic bronchitis, emphysema, influenza, avian influenza, bronchitis, bronchiectasis, pneumonitis, pneumonia, bronchopulmonary dysplasia (BPD), chronic obstructive pulmonary disease (COPD), chronic obstructive airway disease (COAD), acute respiratory distress syndrome (ARDS), chronic respiratory diseases (CRDS), or COVID-19. In some embodiments, the subject at risk may be under the age of 5 or over the age of 60. In some embodiments, the subject may be immunocompromised. In some embodiments, the subject may be hospitalized. In some embodiments, the subject may be pregnant. In some embodiments, the composition delivered to the subject may contain between 0.1 and 600 mg of sodium 2-mercaptoethane sulfonate or 2-mercaptoethylamine. In some embodiments, the composition may contain between 5 and 600 mg of sodium 2-mercaptoethane sulfonate or 2-mercaptoethylamine. In some embodiments, the composition may contain between 20% and 95% by weight (w/w) sodium 2-mercaptoethane sulfonate or 2-mercaptoethylamine. In some embodiments, the composition may include a dry powder. In some embodiments, the composition may include a spray-dried powder. In some embodiments, the composition may be in a liquid form. In some embodiments, sodium 2-mercaptoethane sulfonate or 2-mercaptoethylamine may include 2-mercaptoethane sulfonate or 2-mercaptoethylamine particles. In some embodiments, 2-mercaptoethane sulfonate or 2-mercaptoethylamine particles may be encapsulated. In some embodiments, sodium 2-mercaptoethane sulfonate or 2-mercaptoethylamine particles may be encapsulated in liposomes, microspheres, engineered spray-dried particles, or nanoparticles. In some embodiments, the composition may further include a second anti-viral. In some embodiments, the second anti-viral may include remdesivir, idoxuridine, trifluridine, brivudine, vidarabine, entecavir, telbivudine, foscarnet, zidovudine, didanosine, zalcitabine, stavudine, lamivudine, abacavir, emtricitabine, nevirapine, delavirdine, efavirenz, etravirine, rilpivirine, saquinavir, ritonavir, indinavir, nelfinavir, amprenavir, lopinavir-ritonavir, atazanavir, fosamprenavir, tipranavir, darunavir, telaprevir, boceprevir, simeprevir, asunaprevir, paritaprevir, grazoprevir, raltegravir, elvitegravir, dolutegravir, palivizumab, docosanol, enfuvirtide, maraviroc, varizig, acyclovir, ganciclovir, famciclovir, valacyclovir, penciclovir, valganciclovir, cidofovir, tenofovir disoproxil fumarate, or adefovir dipivoxil. In some embodiments, the composition may further include one or more anti-inflammatory, corticosteroid, antihistamine, bronchodilator, short-acting beta-agonist, long-acting beta-agonist, short-acting muscarinic antagonist, long-acting muscarinic antagonist, immunosuppressant, antibiotic, antiviral, antifungal, anti-infective agent, or any combination thereof. In some embodiments, the composition may further include an anti-inflammatory. In some embodiments, the composition may further include a corticosteroid. In some embodiments, the composition may further include a short-acting beta-agonist. In some embodiments, the composition may further include a long-acting beta-agonist. In some embodiments, the composition may further include a short-acting muscarinic antagonist. In some embodiments, the composition may further include a long-acting muscarinic antagonist. In some embodiments, the composition may further include an immunosuppressant. In some embodiments, the composition may further include an antibiotic. In some embodiments, the composition may further include an antifungal. In some embodiments, the composition may further include an anti-infective agent. In some embodiments, the composition may further include an antihistamine. In some embodiments, the composition may further include a bronchodilator. In some embodiments, the composition may further include mannitol, calcium chloride, magnesium stearate, edetate disodium (EDTA), sodium acetate, dipalmitoylphosphatidylcholine (DPPC), soy lecithin, egg lecithin, hydrogenated soybean phosphatidylcholine (HSPC), cholesterol, PEG (polyethylene glycol); distearoyl-sn-glycero-phosphoethanolamine (DSPE); distearoylphosphatidylcholine (DSPC); dioleoylphosphatidylcholine (DOPC); egg phosphatidylcholine (EPC); DOPS (dioleoylphosphatidylserine); palmitoyloleoylphosphatidylcholine (POPC); sphingomyelin (SM); methoxy polyethylene glycol (MPEG); dimyristoyl phosphatidylcholine (DMPC); dimyristoyl phosphatidylglycerol (DMPG); distearoylphosphatidylglycerol (DSPG); dierucoylphosphatidylcholine (DEPC); dioleoly-sn-glycero-phophoethanolamine (DOPE), triolein, 1,2-distearoyl-sn-glycero-3-phosphoethanolamine sodium salt (MPEG-DSPE), or 1,2-Dipalmitoyl-sn-glycero-3-phosphorylglycerol sodium salt (DPPG).

In another aspect, the invention may provide methods of reducing extracellular disulfide bonds in a viral protein, the method comprising the step of contacting the viral protein with sodium 2-mercaptoethane sulfonate or 2-mercaptoethylamine particles.

In another aspect, the invention may provide methods of reducing extracellular disulfide bonds in a viral protein, the method comprising the step of contacting the viral protein with sodium 2-mercaptoethane sulfonate particles.

In another aspect, the invention may provide methods of reducing extracellular disulfide bonds in a viral protein, the method comprising the step of contacting the viral protein with 2-mercaptoethylamine particles. In some embodiments, the viral protein may include a coronavirus spike protein. In some embodiments, the coronavirus may include SARS-CoV. In some embodiments, the coronavirus may include SARS-COV-2. In some embodiments, the SARS-COV-2 may include a SARS-COV-2 variant. In some embodiments, the variant may include Delta (B.1.617.2, SEQ ID NO: 32-35), Alpha (B.1.1.7, SEQ ID NO: 15-19), Gamma (P.1, SEQ ID NO: 25-31), Beta (B.1.351 SEQ ID NO: 20-24), or Omicron (B.1.1.529). In some embodiments, the disulfide bonds may be reduced by at least 10%, 20%, 30%, 40%, 50%, 60%, 70%, 80%, 90%, or 95%. In some embodiments, the size of the particles may be from 0.01 microns to 15 microns. In some embodiments, the particles may be sized for predominant absorption at a target location of the lung, gastro-intestinal system, kidney, liver, heart, brain, blood-brain barrier (BBB), blood, tissues, central nervous system, lymph nodes, pancreas, gallbladder, diaphragm, reproductive organs, esophagus, colon, or bladder. In some embodiments, the particles may be sized for predominant absorption at a target location of the airways of the subject, wherein the target location may include the upper respiratory track or the lower respiratory track. In some embodiments, the bulk density of the composition may be between 0.1 and 5 g/mL. In some embodiments, sodium 2-mercaptoethane sulfonate or 2-mercaptoethylamine particles may have a median mass aerodynamic diameter between 1 and 8 μm. In some embodiments, the fine particle fraction of the composition less than or equal to a mass median aerodynamic diameter of 6 μm may be between 10 and 90%. In some embodiments, the fine particle fraction of the composition less than or equal to a mass median aerodynamic diameter of 5 μm may be between 10 and 90%. In some embodiments, the fine particle fraction of the composition less than or equal to a mass median aerodynamic diameter of 7 μm may be between 10 and 90%. In some embodiments, the composition may be delivered through the oral, sublingual, parenteral, intravenous, transdermal, or subcutaneous route. In some embodiments, the composition may be delivered through the nose, mouth, trachea, or bronchia. In some embodiments, the composition may be administered nasally, orally, sublingually, intravenously, parenterally, intratracheally, rectally, transdermal, or subcutaneously. In some embodiments, the composition may be administered via inhalation, oral spray, nasal spray, instillation, or nebulization. In some embodiments, the inhalation may include dry powder inhalation. In some embodiments, the subject may be treated at least once per week. In some embodiments, the subject may be treated at least once per day. In some embodiments, the subject may be treated one to four times per day. In some embodiments, the subject may be treated as an out-patient.

These and other aspects and features of nonlimiting embodiments of the present invention will become apparent to those skilled in the art upon review of the following description of specific nonlimiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 1A-D show mutation regions from spike protein amino acid sequences: SARS-CoV-2 (SEQ ID NO: 1-14), A) Alpha (B.1.1.7 SEQ ID NO: 15-19), B) Beta (B.1.351, SEQ ID NO: 20-24), C) Gamma (P.1, SEQ ID NO: 25-31), and D) Delta (B.1.617.2, SEQ ID NO: 32-35) variants, underlining changes in amino acids and highlighting receptor binding domain (RBD) regions;

Figure 2:
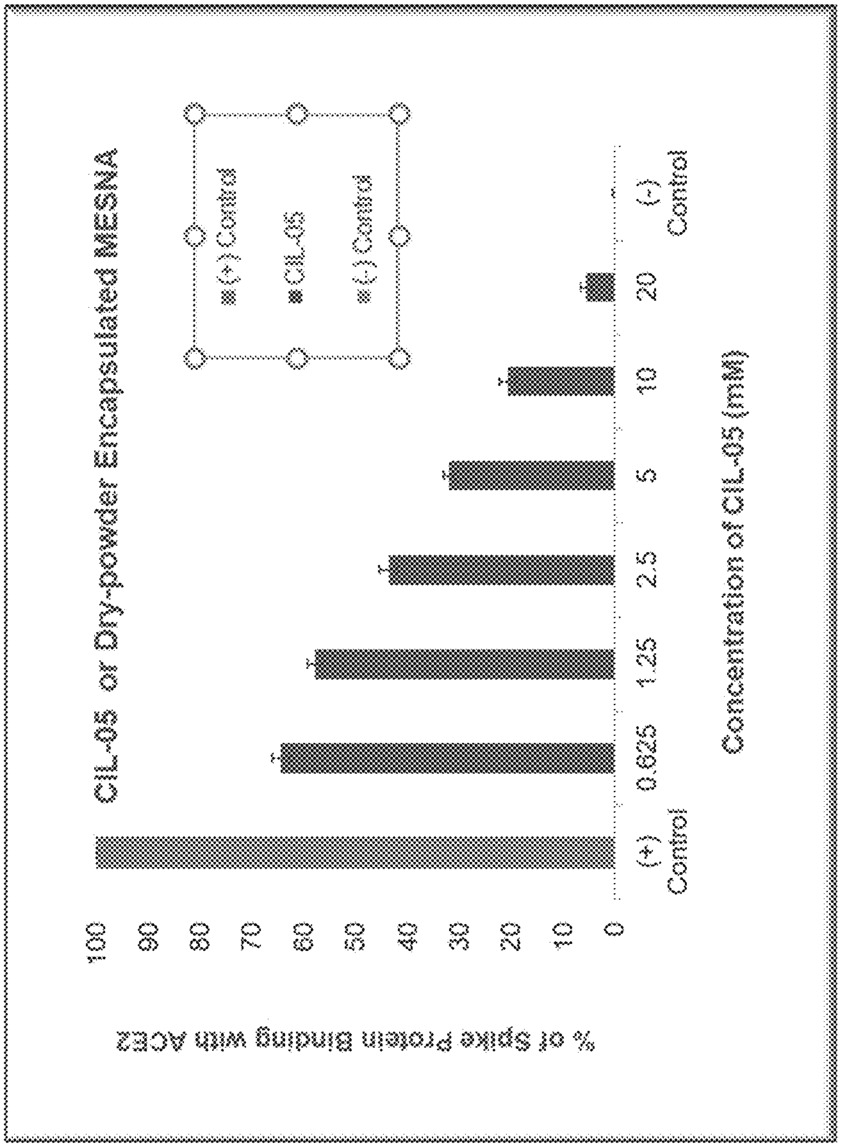
FIG. 2 shows the impact of the present invention on extent (%) of SARS-COV-2 spike protein binding with human angiotensin-converting enzyme 2 (ACE2) receptor when combined with increasing concentrations of a present composition.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to anti-viral therapeutic agents and uses related thereto. Aspects of the present disclosure may be used to prevent and/or treat viral infections. Exemplary embodiments illustrating aspects of the present disclosure are described below in the context of several specific examples.

To facilitate the understanding of this invention, a number of terms are defined below and throughout the disclosure. Unless otherwise defined, all technical and scientific terms used herein have the same meaning as commonly understood by one of ordinary skill in the art to which this invention belongs. The terminology herein is used to describe specific embodiments of the invention, but their usage does not limit the invention, except as outlined in the claims.

Terms such as "a", "an," and "the" are not intended to refer to only a singular entity but include the general class of which a specific example may be used for illustration.

As used herein, the term "about" refers to a value that is within 10% above or below the value being described.

The terms "administration" or "administering" refer to a method of giving a dosage of a compound or pharmaceutical composition to a subject.

As used herein, the terms "pharmacologically effective amount", "therapeutically effective amount", and the like, when used in reference to a therapeutic composition, refer to a quantity sufficient to, when administered to the subject, including a mammal, for example a human, effect beneficial or desired results, such as clinical results. For example, in the context of treating infection, described herein, these terms refer to an amount of the composition sufficient to achieve a treatment response as compared to the response obtained without administration of the composition. The quantity of a given composition described herein that will correspond to such an amount may vary depending upon various factors, such as the given agent, the pharmaceutical formulation, the route of administration, the type of disease or disorder, the identity of the subject (e.g., age, sex, weight) or host being treated, and the like. An "effective amount", "pharmacologically effective amount", or the like, of a composition of the present disclosure, also includes an amount that results in a beneficial or desired result in a subject as compared to a control.

As used herein, the terms "treat", "treating", or "treatment" refer to administration of a compound or pharmaceutical composition for a therapeutic purpose. To "treat a disorder" or use for "therapeutic treatment" refers to administering treatment to a patient already suffering from a disease to ameliorate the disease or one or more symptoms thereof to improve the patient's condition (e.g., by reducing one or more symptoms of inflammation). The term "therapeutic" includes the effect of mitigating deleterious clinical effects of certain inflammatory processes (i.e., consequences of the inflammation, rather than the symptoms of inflammation). The methods of the invention can be used as a primary prevention measure, i.e., to prevent a condition or to reduce the risk of developing a condition. Prevention refers to prophylactic treatment of a patient who may not have fully developed a condition or disorder, but who is susceptible to, or otherwise at risk of, the condition. Thus, in the claims and embodiments, the methods of the invention can be used either for therapeutic or prophylactic purposes.

Other features and advantages of the invention will be apparent from the Detailed Description, Examples, Figures, and Claims.

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, and/or components have not been described in detail in order to avoid unnecessarily obscuring claimed subject matter. The illustrative embodiments described in the detailed description and claims are not meant to be limiting. Other embodiments may be utilized, and other changes may be made, without departing from the spirit or scope of the subject matter presented here. It will be readily understood that the aspects of the present disclosure, as generally described herein, can be arranged, substituted, combined, and designed in a wide variety of different configurations, all of which are explicitly contemplated and make part of this disclosure.

Without limiting the scope of the invention, the present invention is related to anti-viral activity of therapeutic agents. International Patent Application No. PCT/US2021/047774, incorporated herein by reference, describes exemplary therapeutic agents which the inventors have now discovered may be used to reduce the risk of and/or treat viral infections.

Viral Infections

In some embodiments, the present invention may be directed to a method of reducing the risk of a viral respiratory infection in a subject at risk of an infection or treating the subject after the onset of infection. The present compositions may reduce the risk of a viral infection in a subject at risk and treat a range of viral respiratory infections.

In some embodiments, the present invention may be directed to the reduction of risk of and treatment of diseases caused or worsened by viral respiratory infections, e.g., coronavirus; severe acute respiratory syndrome (SARS); the Middle East Respiratory Syndrome (MERS); severe acute respiratory syndrome coronavirus 2 (SARS-CoV-2), the cause of COVID-19 disease; rhinovirus, the common cold virus; respiratory syncytial virus (RSV); avian influenza viruses; influenza A, B, and C viruses; adenoviruses; herpesviruses; human papillomaviruses; parvoviruses; reoviruses: picornaviruses; coronaviruses; flavivirus; togaviruses, orthomyxovirus: bunyaviruses; rhabdoviruses; paramyxoviruses; pneumonia; conjunctivitis; gastroenteritis; pharyngitis; acute hemorrhagic cystitis; herpes simplex virus; varicella zoster virus; Epstein-Barr virus; HPV types 1-65; parvovirus B 19; canine parvovirus; orbivirus; rotavirus; aquarcovirus; coltivirus; enterovirus; hepatovirus; coronavirus and torovirus; petsiviras; hepatitis C-like viruses; alphavirus; rubivirus; Thogoto virus; Hantavirus; Nairovirus; phlebovirus; rabies virus; ephemerovirus; vesiculovirus; measles virus; mumps virus; etc. through the use of oral, inhalable, intranasal, parenteral, rectal, dermal, and/or nebulized anti-viral compositions.

In some embodiments, present invention may be directed to the reduction of risk of and treatment of diseases caused or worsened by viral respiratory infections, wherein the viral infection is from a virus family selected from the group consisting of Herpesviridae, Papillomaviridae, Polyomaviridae, Poxviridae, Anelloviridae, Circoviridae, Genomoviridae, Parvoviridae, Hepadnaviridae, Retroviridae, Picobirnaviridae, Reoviridae, Coronaviridae, Astroviridae, Caliciviridae, Flaviviridae, Matonaviridae, Hepeviridae, Picornaviridae, Togaviridae, Filoviridae, Paramyxoviridae, Pneumoviridae, Rhabdoviridae, Arenaviridae, Hantaviridae, Nairoviridae, Peribunyaviridae, Phenuiviridae, and Orthomyxoviridae.

Severe Acute Respiratory Syndrome Coronavirus 2 (SARS-COV-2)

Coronavirus disease 2019 (COVID-19), caused by SARS-CoV-2 infection, is a global pandemic with greater than 252 million confirmed cases and greater than five million deaths worldwide. In the US there have been more than 46 million confirmed cases and greater than 760,000 deaths. In addition to human loss, the pandemic has been described by International Monetary Fund (IMF) the cause of a global decline on the scale of the Great Depression of the 1930s. The global economy contracted by 3.5% with specific region economy and unemployment rates increased dramatically.

The clinical presentation of COVID-19 is heterogeneous, ranging from asymptomatic to severe respiratory failure leading to mechanical ventilation and/or death. The pathology of serious SARS-CoV-2 lung infection is characterized by neutrophil inflammation, mucous plug with fibrinous exudate in the alveoli, alveolar damage and microthrombi.

Elderly individuals and patients with underlying lung diseases have a significantly increased risk of severe COVID-19 because of their diminished immune response and ability to repair the damaged epithelium. Reduced muco-ciliary clearance also contributes to viral spread to the gas exchange units more readily. The airway blockage with mucus produces regional hypoxia and necrosis of airway epithelial cells. Necrotic epithelial cells lead to neutrophilic inflammation even in the absence of infection.

In August of 2020 the Food and Drug Administration (FDA) approved the first COVID-19 vaccine from Pfizer-BioNTech for the prevention of COVID-19 disease in individuals 16 years of age and older. The approval of the Pfizer-BioNTech vaccine was followed by 3 other vaccines from Moderna, Astra Zeneca, and Johnson & Johnson. As the vaccination rate increased, a decline in COVID-19 cases occurred. However, there has been a rise in new variants of the virus that are more contagious, causing widespread disease, hospitalization, and death, against which the currently available vaccines have less effectiveness, as well as breakthrough infections in vaccinated subjects.

Coronavirus is a family of the viruses and can cause illness such as the common cold, severe acute respiratory syndrome (SARS), the Middle East Respiratory Syndrome (MERS) and COVID-19 infection.

The SARS-COV-2 genome encodes four structural proteins, Nucleocapsid (N) protein, Membrane (M) protein, spike (S) protein, and Envelop (E) protein, as well as several non-structural proteins. The S-protein is integrated over the surface of the virus and mediates attachment of the virus to the host cell surface receptors and fusion between the viral and host cell membranes to facilitate viral entry into the host cell. The virus utilizes the coronavirus spike (S) glycoprotein protein receptor binding domain (RBD), with S1 and S2 subunits in each spike monomer, to attach itself to a common human angiotensin converting enzyme 2 (ACE2) receptor that is found on the outer membrane of many human cells, including those in the respiratory apparatus, such as nose, throat, and lungs.

The binding between SARS-COV-2 and the ACE2 receptor initiates a cascade of events resulting in the fusion between cell and viral membranes for cell entry. As binding to the ACE2 receptor is a critical first step for SARS-COV-2 to enter into target cells, the vaccines and therapeutics discovery efforts are focused on blocking this binding.

The ACE2 receptor on the surface of epithelial cells also meditates the entry of severe acute respiratory syndrome coronavirus 1 (SARS-CoV), the virus resulting in severe acute respiratory syndrome commonly known as SARS. However, SARS-CoV-2 binding to ACE2 is 2-4 times stronger than that of SARS-CoV. The increase in binding strength is believed to be due to the differences in the sequence of spike protein resulting in a stabilized RBD that is readily recognized by the receptor.

Viruses often change through mutation. A variant of the original virus occurs when the virus has one or more new mutations in their amino acid sequence. Since March 2020, several new genetic variants of SARS-COV-2 with varying degrees of pathogenicity have appeared. World Health Organization (WHO) has declared four of those as "variants of concern (VOC)". The Center for Disease Control (CDC)

defines the variant of concern as a variant with specific genetic markers that have been associated with changes to receptor binding, reduced neutralization by antibodies generated against previous infection or vaccination, reduced efficacy of treatments, potential diagnostic impact, or predicted increase in transmissibility or disease severity.

The SARS-COV-2 variants that are currently in circulation and causing concern in the United States include:

- Delta (B.1.617.2, SEQ ID: 32-35): The delta variant was identified in India in October of 2020 and gained dominance quickly after it was first reported in the United States in March 2021. This variant is now the most common COVID-19 variant in the United States. The delta variant is nearly twice as contagious as earlier variants and may cause more severe illness. The greatest risk of transmission of the delta variant is among unvaccinated people. However, fully vaccinated individuals with breakthrough infections accompanied by symptoms can also spread the virus to others. The delta variant may also reduce the effectiveness of some monoclonal antibody treatments and the antibodies generated by a COVID-19 vaccine.
- Alpha. (B.1.1.7, SEQ ID NO: 15-19): The alpha strain first appeared in Great Britain. The alpha variant of COVID-19 appears to spread more easily, with about a 50% increase in transmission compared to previous circulating variants. The alpha variant also may have an increased risk of hospitalization and death.
- Gamma (P.1, SEQ ID NO: 25-31): The gamma strain first surfaced in Brazil. The gamma variant reduces the effectiveness of some monoclonal antibody medications and the antibodies generated by a previous COVID-19 infection or a COVID-19 vaccine.
- Beta (B.1.351, SEQ ID NO: 20-24): The beta strain first surfaced in South Africa. The beta variant appears to spread more easily, with about a 50% increase in transmission compared to previous circulating variants. It also reduces the effectiveness of some monoclonal antibody medications and the antibodies generated by a previous COVID-19 infection or COVID-19 vaccine.
- Omicron (B.1.1.529): The omicron strain was first detected in South Africa. The omicron variant includes a high number of variants, increasing the risk of spread, seriousness of disease, and reduction in effectiveness of some monoclonal antibody medications and the antibodies generated by a previous COVID-19 infection or COVID-19 vaccine.

Referring now to FIGS. 1A-D, FIGS. 1A-D show mutation regions from spike protein amino acid sequences: SARS-CoV-2 (SEQ ID NO: 1-14), A) Alpha (B.1.1.7, SEQ ID NO: 15-19), B) Beta (B.1.351, SEQ ID NO: 20-24), C) Gamma (P1, SEQ ID NO: 25-31), and D) Delta (B.1.617.2, SEQ ID NO: 32-35) variants highlighting RBD regions. FIGS. 1A-D further show the alignment of 60 consecutive amino acids residues from the spike protein where mutations have occurred.

The mutations in the virus's spike protein are responsible for the degree of severity of the resulting disease of the variants. The mutations in the RBD of the spike protein may enable the virus to bind more tightly to human receptors and become more contagious, enabling the virus to re-infect someone who has previously been exposed or infected and possibly evade the immune response in a subject who has been vaccinated. These infections are often described as break-through infections.

The present compositions may be effective independent of virus mutation. Without being bound to theory, the present compositions disrupt both the virus's disulfide bridge and hydrogen bond, as well as other non-valent interactions of the RBD of the virus spike protein, altering the three-dimensional structure of the RBD. The present compositions may also alter the extracellular binding site of the receptor. The changes in the three-dimensional structure of the virus spike protein may lead to further reduction in binding affinity, and therefore a reduction of entry of the virus into the cell via the receptor-mediated mechanism.

Variants with new mutations may present a significant problem as they have shown to reduce the effectiveness of some antibody treatments. Given that mutations are likely to continue, therapeutics that are mutation agnostic and can inhibit the binding of spike protein RBD with host cell receptor for all variants are critically needed in the field and would benefit all patients.

Targeting the spike proteins by via small molecules and broad-neutralizing antibodies to reduce the binding of RBD with the host receptor may offer a method of treating and reducing the risk of further infections of COVID-19. The objective of the present invention is to reduce the risk of and treat viral infections in subjects regardless of virus mutations. The present compositions may achieve this objective by altering the structure of the viral protein irrespective of the mutation in specific amino acid residues.

In some embodiments, the present invention may reduce the risk of a viral infection in a subject at risk or treats a viral infection of a subject, wherein the viral infection is coronavirus. In some embodiments, the coronavirus may include SARS-CoV. In some embodiments, the coronavirus may include SARS-COV-2 (SEQ ID NO: 1-14). In some embodiments, the viral infection may include a SARS-COV-2 variant. In some embodiments, the viral infection may include a SARS-COV-2 variant, such as Delta (B.1.617.2, SEQ ID NO: 32-35), Alpha (B.1.1.7, SEQ ID NO: 15-19), Gamma (P.1, SEQ ID NO: 25-31), Beta (B.1.351, SEQ ID NO: 20-24), or Omicron (B.1.1.529).

Rhinovirus

Multiple viruses including Rhinovirus and Respiratory Syncytial Virus (RSV) are responsible for pulmonary exacerbations, emergency room visits, and hospitalizations. Rhinovirus, the common cold virus, causes upper respiratory tract symptoms in both children and adults. Rhinovirus is also the most identified virus associated with pulmonary exacerbations in patients with chronic respiratory disease, such as chronic obstructive pulmonary disease (COPD), asthma, cystic fibrosis. Pulmonary exacerbations are characterized by increased respiratory symptoms (cough, wheeze, sputum production, dyspnea) and can result in emergency room visits (COPD: 1.5 million per year, asthma: 1,725,000 per year in US) and hospitalization (COPD: 726,000 per year, asthma: 500,000 per year in US).

There are >160 types of rhinoviruses, with three genetically distinct groups: RV-A, RV-B, RV-C. Most respiratory disease is caused by RV-A and RV-C. Rhinovirus can also be classified by the cellular surface receptor used for entry into respiratory epithelial cells. The majority of RV-A and RV-B use intercellular adhesion molecule-1 (ICAM-1) as their receptor. Some RV-A use low density lipoprotein receptor (LDLR) family members. RV-C uses cadherin related family member 3 (CDHR3). The three-dimensional structure of these receptor proteins is stabilized via intra-protein Cys-Cys disulfide linkages, hydrogen bonds, and other electrostatic linkages formed between amino acid residue as result of specific protein folding. This three-dimensional structure enables the presentation of specific sites to be recognized and bind with the receptor and facilitate its transport into the host cell. All three rhinovirus receptors are characterized by extracellular domains. These domains are coiled and achieve their configuration through Cys-Cys disulfide linkages. Viral surface proteins form specific binding sites that are recognized by these domains of the host cell receptors resulting in cell attachment. Changes in the three-dimensional structure of virus protein and/or the extracellular domains of the host cell receptor can impact the ability of virus to enter the host cell and therefore affects the infectivity and pathogenicity of the virus.

Respiratory Syncytial Virus (RSV)

Respiratory syncytial virus (RSV) is a leading cause of upper and lower respiratory tract disease in young children and elderly people. Despite that the virus was identified in 1955, and efforts from public institutions and multiple biotechnology companies, an effective RSV vaccine is yet to be developed. Currently the only approved intervention is a humanized monoclonal antibody for passive immunoprophylaxis in premature and high-risk infants. RSV respiratory infection is the most common cause of hospitalization of infants and children in the developed world. Globally, RSV is responsible for ~60,000 in-hospital deaths annually in children younger than 5 years of age. RSV can infect almost every child by the age of 2, with two percent of infants developing severe disease. Beyond childhood, the CDC estimates that 177,000 older adults are hospitalized each year due to RSV infection.

RSV has an attachment protein G on its surface that binds to the host cell surface receptor CX3CR1. A soluble form of the G protein is used for immune evasion. The G fusion protein has a critical hairpin configuration (supported via Cys-Cys disulfide bonds) that is necessary for RSV entry into the host cell. Another RSV surface protein, the F protein, facilitates host cell attachment (binding to ICAM-1 amongst other receptors) to the domains and plays an essential role in viral fusion with the host cell. Its configuration also depends upon critical Cys-Cys disulfide linkages. Changes to the three-dimensional structure of the G and F proteins will impact the ability of RSV to enter host cells and therefore the pathogenicity of RSV.

In some embodiments, the present invention reduces the risk of a viral infection in a subject at risk or treats a viral infection of a subject, wherein the viral infection is due to Rhinovirus. In some embodiments, the present invention reduces the risk of a viral infection in a subject at risk or treats a viral infection of a subject, wherein the viral infection is due to RSV.

Subjects at Risk

The present invention may include methods for reducing the risk of viral infections in "at risk" subjects. A subject at risk may be a subject more easily susceptible to acquiring a viral infection, or one who may be more likely to get severely ill from a viral infection. Severe illness may mean person who may need hospitalization, intensive care, oxygen or a ventilator to help them breath, and can potentially result in death.

In some embodiments, the subject at risk may be diagnosed with a medical condition or a pre-existing condition. The subject at risk may be diagnosed with cancer, a kidney disease, a lung or respiratory airway disease, dementia, or other neurological conditions, diabetes (type 1 or type 2), trisomy 21, hypertension, a heart condition, a human immunodeficiency virus (HIV) infection, acquired immunodeficiency syndrome (AIDS), an immunocompromised state, a liver disease, sickle cell disease or thalassemia, stroke or cerebrovascular disease. The subject at risk may be pregnant. The subject at risk may be overweight. The subject at risk may be obese, e.g., a body mass index (BMI) over 40. The subject at risk may be a current or former smoker. The subject at risk may be the subject of a solid organ or blood stem cell transplant. The subject at risk may have a substance use disorder. The subject at risk may have a disability. The subject at risk may be diagnosed with a chronic disease or condition. The subject at risk can be a person being treated with immunosuppressant drugs for unrelated illness.

Subjects at risk may be diagnosed with a lung or respiratory airways disease. Conditions and diseases that may benefit from the present invention include: asthma, primary ciliary dyskinesia (PCD), cystic fibrosis (CF), bronchiectasis (BE), bronchopulmonary Dysplasia (BPD), sinusitis, rhinosinusitis, bronchiolitis obliterans (BO), emphysema, bronchitis, pneumonia, pneumonitis, chronic obstructive pulmonary disease (COPD), other lung and airways diseases, other muco-obstructive diseases, chronic obstructive airway disease (COAD), acute respiratory distress syndrome, chronic respiratory distress, viral and bacterial infections of lungs, and sinus and car diseases.

In some embodiments, the subject at risk may be classified as at risk due to age. The elderly are at higher risk than the overall population. The subject at risk may be over the age of 65. Children are at a higher risk than the overall population for acquiring some viruses, such as RSV. The subject at risk may be under the age of 5. The subject at risk may be premature neonate. Subjects with underlying diseases as listed above are at risk across the age spectrum.

In some embodiments, the subject at risk may be classified as at risk due to housing conditions, professional exposure, or other environmental factors. For example, the subject at risk may be a nursing home resident or the subject at risk may work in the field of healthcare.

Anti-Viral Compositions

The present invention is directed to methods of reducing the risk of viral infection in a subject at risk of a viral infection or treating a viral infection of a subject.

The present invention has stabilized therapeutic activity, reduced expected dose, potential for sustained release, and potential for combination with other molecules, without pre-delivery interactions. These advantages are explained in detail below.

The present invention provides methods of reducing the risk of viral infection in a subject at risk of a viral infection or treating a viral infection of a subject. The method includes the step of administering to the subject a composition containing sodium 2-mercaptoethane sulfonate or 2-mercaptoethylamine.

In some embodiments, the anti-viral agent may include sodium 2-mercaptoethane sulfonate. Without being bound to theory, sodium 2-mercaptoethane sulfonate may be advantageous in that it has a unique chemical structure that can alter the three-dimensional structure of viral proteins, diminish or block the binding of a virus, and prevent the virus from entering into host cell. Sodium 2-mercaptoethane sulfonate has an additional terminal charged sulfonate group with hydrophilic properties that can break the hydrogen bonds and disulfide linkages in viral proteins.

In the SARS-COV-2, the RBD of spike protein includes four Cys-Cys pairs of disulfide linkages that stabilize the three-dimensional structure and binding site of the RBD; three of those are in the core (Cys336-Cys361, Cys379-Cys432 and Cys391-Cys525) that serve to stabilize the β sheet structure. The fourth pair (Cys480-Cys488) in the contact region of RBD and connects the loops in the distal end of the receptor-binding motif (RBM).

Furthermore, there are also a number of electrostatic hydrogen bonds that help stabilize the structure of the RBD necessary for being recognized by the ACE-receptor. The N-terminal peptidase domain of ACE2 has two lobes that form the binding site therebetween. The extended RBM in the SARS-COV-2 RBD contacts the bottom side of the small lobe of ACE2, with a concave outer surface in the RBM that accommodates the N-terminal helix of the ACE2.

Without being bound to theory, sodium 2-mercaptoethane sulfonate, combining a terminal free thiol group and a terminal charged sulfonate group, may offer dual action for altering the structure of the SARS-COV-2 spike protein. The free thiol group of sodium 2-mercaptoethane sulfonate may break the four Cys-Cys disulfide linkages in the RBD, and the charged sulfonate group may disrupt hydrogen bonds and other non-covalent links that help stabilize RBD structure to be recognized with ACE2 receptor. This combination of actions may modify the three-dimensional structure of the RBD of spike protein and impact its ability to bind with the ACE2 receptor.

The Cys-Cys pairs are conserved in all variants of SARS-COV-2. Therefore, sodium 2-mercaptoethane sulfonate may inhibit the binding in a mutation agnostic manner. Furthermore, and without being bound to theory, the ability of sodium 2-mercaptoethane sulfonate to scavenge the reactive oxygen species in the airways offers additional benefit of reducing oxidative stress.

The present invention may provide methods of reducing the risk of viral infection in a subject at risk or treating viral infection of a subject, the method comprising administering to the subject a composition comprising sodium 2-mercaptoethane sulfonate particles. The present invention may also provide methods of reducing the risk of viral infection in a subject at risk or treating viral infection of a subject, the method comprising administering to the subject a composition comprising sodium 2-mercaptoethane sulfonate particles.

In some embodiments, the anti-viral agent is 2-mercaptoethylamine, also known as cysteamine. Without being bound to theory, 2-mercaptoethylamine may also break the disulfide linkages and extracellular components of viral proteins, resulting in altered three-dimensional structure of the receptor binding domain. In the process, 2-mercaptoethylamine may form cysteine-cysteamine mixed disulfide linkages. 2-mercaptoethylamine may also promote the transport of L-cysteine into cells, which may be further used to synthesize glutathione, a potent intracellular antioxidant that serves to scavenge reactive oxygen species and serve as an anti-inflammatory. Thus, 2-mercaptoethylamine may simultaneously reduce the rate of viral entry while also reducing inflammation caused by reactive oxygen species. The present invention may provide methods of reducing the risk of viral infection in a subject at risk or treating a viral infection of a subject, the method comprising administering to the subject a composition comprising 2-mercaptoethylamine particles.

Composition Forms

In some embodiments, the present compositions may be in dry powder form. Dry powder formulations may offer several advantages, including improved stability (such as at room temperature) and case of storage and transportation. Dry powder formulations are easy to inhale, rapid to administer, portable, and have low risk of infection. In some embodiments, delivery via inhalation may also reduce the risk of side effects. In some embodiments, the dry powder compositions may be produced using spray-drying. In some embodiments, the present compositions may include spray-dried powders. In some embodiments, the dry powder compositions may be reconstituted into a liquid form prior to administration.

In some embodiments, the present compositions may be in liquid form. In some embodiments, the present compositions may be solubilized and reconstituted in solution for the administration, e.g., via nebulization or instillation to children under the age of 5 or ventilated patients. Nebulization and instillation may be advantageous for administration to children and ventilated patients.

Excipients

In some embodiments, the present compositions may include one or more excipients. For the purposes of this disclosure, an "excipient" is an inactive substance included in a pharmaceutical formulation to support the manufacturing process of a drug and/or to enhance the performance, stability, and/or usability of a drug. As nonlimiting examples, excipients may serve functions such as binders, fillers, disintegrants, lubricants, preservatives, and flavoring agents, ensuring proper delivery and absorption of one or more active ingredients. Excipients may be critical in drug formulation for improving an overall effectiveness and patient acceptability of a medication.

In some embodiments, the present invention may be directed to inhalable and/or intranasal compositions including an anti-viral agent and one or more excipients, as well as methods of reducing the risk of viral infections in a subject at risk or treating a viral infection of a subject, the method including administering via inhalation to the subject a composition including an anti-viral agent and one or more excipients.

Exemplary excipients may include mannitol, magnesium stearate, sodium acetate, calcium chloride, soy lecithin; egg lecithin; hydrogenated soybean phosphatidylcholine (HSPC); cholesterol, polyethylene glycol (PEG); dipalmitoylphosphatidylcholine (DPPC); DSPE (distearoyl-sn-glycero-phosphoethanolamine); DSPC (distearoylphosphatidylcholine); DOPC (dioleoylphosphatidylcholine); EPC (egg phosphatidylcholine); DOPS (dioleoylphosphatidylserine); POPC (palmitoyloleoylphosphatidylcholine); SM (sphingomyelin); MPEG (methoxy polyethylene glycol); DMPC (dimyristoyl phosphatidylcholine); dimyristoyl phosphatidylglycerol (DMPG); DSPG (distearoylphosphatidylglycerol); dierucoylphosphatidylcholine (DEPC); dioleoly-sn-glycero-phophoethanolamine (DOPE); triolein; 1,2-distearoyl-sn-glycero-3-phosphoethanolamine sodium salt (MPEG-DSPE); phosphatidylcholine (PC); and 1,2-Dipalmitoyl-sn-glycero-3-phosphorylglycerol sodium salt (DPPG). In some embodiments, the excipient may be phospholipid based, which are part of lung surfactants and thus compatible with a lung environment.

In some embodiments, excipients may make up less than 50% of a total composition, e.g., less than 50%, less than 40%, less than 30%, less than 20%, less than 10%, less than 5%, or less than 1%. In some embodiments, the excipients may make up between 1% and 50% of a total composition, e.g., 1% to 10%, 10% to 20%, 20% to 30%, 30% to 40%, or 40% to 50%.

Administration

The present invention encompasses therapeutic agents and methods for reducing the risk of viral infection in a subject at risk or treating viral infection of a subject by administration of the present compositions. The present compositions may be administered nasally, orally, sublingually, intravenously, parenterally, intratracheally, rectally, transdermal, or subcutaneously.

In some embodiments, the present compositions may be delivered to the subject through direct pulmonary administration through any one or more of the routes including the nasal, oral, intratracheal, and bronchial instillation. The present invention, as an inhalable and/or intranasal anti-viral, may offer multiple advantages, including direct delivery to nasal and oral passages for certain viruses that use these routes to enter the upper and/or lower respiratory tract, the ability to reach viruses present in lower part of the respiratory tract, and the ability to reach the site of airway mucus plugs that may cause inflammation and airway blockage. In some embodiments, the present compositions may be formulated for depositing on an airway surfactant layer and may offer delayed absorption by an airway surface, resulting in a prolonged retention at the airway surface.

In some embodiments, the present compositions may be delivered by means of administering inhalable and/or intranasal liposomes, microspheres, engineered spray-dried particles, or nanoparticles directly to lungs and the respiratory tract.

In some embodiments, the present compositions may be deployed by intranasal route, direct instillation, dry powder inhalation, wet nebulized-inhalation, or aerosolized inhalation via airways route.

The methods for delivery by inhalation or the intranasal route envision the use of a dispersing apparatus such an inhaler, e.g., a dry powder inhaler; a low-resistance inhaler such as a capsule-based monodose low-resistance inhaler device; a nasal spray device; a dropper; a nebulizer, such as a handheld portable nebulizer; or a compressor-nebulizer inhaling device capable of delivering drug-encapsulating particles via the inhaled and/or intranasal route. In some embodiments, a dispersing apparatus may be used such that a product becomes easy to inhale, even for those with an advanced respiratory disease.

An exemplary device compatible with the present compositions is the RS01 Monodose inhaler, e.g., with size #2 and/or #3 capsule packaged individually. The monodose inhaler may be advantageous in that drug particles may reach deep lungs even for patients with breathing difficulties, as the device offers both low resistance and works well with a flow rate of 15-20 L/min-100 L/min, depending on a patient's ability to inhale. Particles of the present compositions may be filled into size #3 capsules as desired for potency and fill weight. Exemplary fill weights may be less than 40 mg, e.g., less than 30 mg, less than 25 mg, less than 20 mg, less than 15 mg, less than 10 mg, less than 5 mg, or less than 1 mg. The above described may then be inhaled (e.g., using a Plastiape DPI (RS01) or other inhaler or nebulizer) at a flow rate of 15-60 L/min by a patient (i.e, a slow and deep inhalation).

In some embodiments, the compositions may be administered with an intratracheal device.

In some embodiments, the formulation may include or be included in a prescription drug, which may be advantageous in that it does not require hospitalization or clinical setting for administration because of quick and convenient delivery anywhere, e.g., at home, via an inhaler for patient's convenience.

In some embodiments, the compositions may be administered at least once a week, e.g., every other day, once a day, twice a day, three times a day, etc. In some embodiments, the compositions may be administered one to four times a day. In some embodiments, the compositions may be administered at least once a day. In some embodiments, the compositions may be administered at least twice a day. In some embodiments, the compositions may be administered at least three times a day.

In some embodiments, the compositions may be administered for at least three days, e.g., at least four days, at least five days, at least six days, at least seven days, at least eight days, at least nine days, at least ten days, at least eleven days, at least twelve days, at least thirteen days, or at least fourteen days.

In some embodiments, the invention may include a method of reducing the risk of a viral infection in a subject at risk, the method including administering to the subject a composition including a thiol-based particle. Thiol-based particle may include sodium 2-mercaptoethane sulfonate or 2-mercaptoethylamine particles. For the purposes of this disclosure, a "thiol" is a molecule containing a —SH functional group. Thiol may include sodium 2-mercaptoethane sulfonate or 2-mercaptoethylamine. In some embodiments, the method may include administering the composition at least once per day. In some embodiments, the method may include administering the composition at least twice per day. In some embodiments, the method may include administering the composition at least three times per day. In some embodiments, the method may include administering the composition for at least three days. In some embodiments, the method may include administering the composition for at least five days. In some embodiments, the method may include administering the composition for at least seven days.

In some embodiments, the present invention may include a method of treating a viral infection in a subject, the method including administering to the subject a composition including thiol-based particles. Thiol-based particles may include sodium 2-mercaptoethane sulfonate or 2-mercaptoethylamine particles. In some embodiments, the method may include administering the composition at least once per day. In some embodiments, the method may include administering the composition at least twice per day. In some embodiments, the method may include administering the composition at least three times per day. In some embodiments, the method may include administering the composition for at least three days. In some embodiments, the method may include administering the composition for at least five days. In some embodiments, the method may include administering the composition for at least seven days.

Dosing

A multitude of doses of composition are included herein. In some embodiments, the composition delivered to the subject may be from about 5 mg to about 600 mg, e.g., 5 to 50 mg, 5 to 100 mg, 50 to 100 mg, 100 to 150 mg, 100 to 300 mg, 100 to 400 mg, 100 to 500 mg, 150 to 200 mg, 200 to 250 mg, 200 to 400 mg, 200 to 500 mg, 250 to 300 mg, 300 to 350 mg, 350 to 400 mg, 400 to 450 mg, 400 to 500 mg, 400 to 600 mg, 450 to 500 mg, 500 to 550 mg, 500 to 600 mg, or 550 to 600 mg. Doses of anti-viral agent of greater than 5 mg are included herein, e.g., greater than 10 mg, greater than 15 mg, greater than 20 mg, greater than 25 mg, greater than 30 mg, greater than 35 mg, greater than 40 mg, greater than 45 mg, greater than 50 mg, greater than 60 mg, greater than 70 mg, greater than 80 mg, greater than 90 mg, greater than 100 mg, greater than 125 mg, greater than 150 mg, greater than 175 mg, greater than 200 mg, greater than 250 mg, greater than 300 mg, greater than 350 mg, greater than 400 mg, greater than 450 mg, greater than 500 mg, or greater than 550 mg.

A multitude of anti-viral loadings in the compositions are included herein. Anti-viral loading in the present compositions may be from about 50-99% of the total composition, e.g., 50% to 60%, 50% to 70%, 50% to 75%, 50% to 80%, 50% to 90%, 60% to 70%, 60% to 80%, 60% to 90%, 70% to 80%, 70% to 90%, 80% to 90%, 90% to 95%, or 90% to 100%.

The present compositions may include greater than 50% by total weight anti-viral agent, e.g., greater than 50%, greater than 60%, greater than 70%, greater than 80%, greater than 90%, greater than 95%, greater than 99% or greater than 99.9%.

Target Locations

In some embodiments, the particles of the present compositions may be sized for predominant absorption at a target location. The particles of the present invention may be formulated to absorb into a target location of a human body, thus targeting a viral infection.

In some embodiments, the particles may be sized for predominant absorption at a target location of the lung, gastro-intestinal system, kidney, liver, heart, brain, blood-brain barrier (BBB), blood, tissues, central nervous system (CNS), lymph nodes, pancreas, gallbladder, diaphragm, reproductive organs, esophagus, colon, or bladder.

In some embodiments, the particles may be sized for predominant absorption at a target location of the airways of the subject, wherein the target location is the upper respiratory track or the lower respiratory track.

Encapsulation

In some embodiments, the compositions may be in the form of encapsulated particles.

In some embodiments, the formulations may stabilize oxidative activity of thiol agents, such as the monomeric form of sodium 2-mercaptoethane sulfonate, preventing potential loss of therapeutic activity. In some embodiments, the present compositions may be configured to stabilize the active monomeric state of sodium 2-mercaptoethane sulfonate.

In some embodiments, the thiol group of the sodium 2-mercaptoethane sulfonate may be kept from dimerization via disulfide linkage. However, in some instances, and without being bound to theory, sodium 2-mercaptoethane sulfonate may autoxidize in oxygen rich environments to form a dimer, di-sodium 2-mercaptoethane sulfonate, resulting in potential loss of therapeutic activity.

Thus, the present invention may offer an advantage of stabilized anti-viral activity without pre-delivery interaction. In some embodiments, sodium 2-mercaptoethane sulfonate may be stabilized with an encapsulation of the particles, such as microsphere, spray-dried, liposome, or nanoparticle encapsulations, in order to increase the ability of the sodium 2-mercaptoethane sulfonate to break disulfide linkages and other electrostatic interactions of viral proteins. Further, the stability of the encapsulated particles may enable the use of standard supply chain, as opposed to requiring specialized and costly cold-chain supply methods.

Furthermore, encapsulation of active pharmaceutical ingredients may be a useful method for targeted drug delivery. Without wishing to be bound by theory, liposome formulations may be used to deliver pharmaceuticals to specific locations, and release them at specific times, as demonstrated in U.S. Pat. No. 4,797,285 herein incorporated by reference in its entirety. Liposomes, microspheres, engineered spray-dried particles, and nanoparticles represent unique drug carriers that can site-specifically deliver the drug directly to the respiratory tract while protecting it from interaction with environment (such as blood, metabolism, exposure to air, etc.).

As such the present encapsulation vehicles may be advantageous for protecting the anti-viral agents, alone or when in combination with other therapies, from pre-delivery conversion to its metabolites, thus preserving its potency until the drug is released at the target site.

Microspheres encapsulating active pharmaceutical compounds may include polymers (e.g., polyethylene glycol, polylactide, polyhydroxybutyrate, or polycaprolactone), or copolymers (e.g., polyethylene glycol-polylactide block copolymer). An exemplary method to form microspheres may involve dissolving the active pharmaceutical ingredient in a non-aqueous solvent, forming an oil-in-water emulsion with the solution, followed by volatilizing the organic solvent. In some embodiments, microsphere compositions are spray dried. U.S. Pat. No. 7,011,776 demonstrates the use of microspheres and is incorporated herein by reference in its entirety.

Spray-dried particles, also known as engineered spray-dried particles, may be formed in a process in which a mixture of active pharmaceutical compound and carrier is injected into a hot gas stream, thereby forming fine droplets. The mixture may be a solution, suspension, slurry, or similar. As the solvent evaporates, individual dry particles on the order of single micron in diameter are formed. Further details on the methods of formation of these engineered spray-dried particles are demonstrated in U.S. Pat. Nos. 6,673,335 and 5,993,805, herein incorporated in its entirety.

Nanoparticles may be used as drug carriers for targeted delivery or timed-release of active pharmaceutical compounds. Polymer and co-polymer materials are among those used in preparing nanoparticles for encapsulation. As a nonlimiting example active pharmaceutical ingredients may be encapsulated in nanoparticles via interfacial polymerization. In interfacial polymerization, active pharmaceutical ingredient and polymerizable monomer are dissolved in a non-aqueous solvent, which is added to an aqueous solvent. Polymerization and encapsulation occur at the organic-aqueous interface. Nonlimiting examples of polymerizable monomers include alkylcyanoacrylates (where alkyl is e.g., n-butyl, isobutyl, isohexyl, etc.). Nanoparticle encapsulation may be used to deliver small molecules as well as peptide pharmaceuticals. Further methods and compositions are detailed in U.S. Pat. Nos. 8,3818,208 and 5,641,515, both incorporated by reference.

The advantages of encapsulation of sodium 2-mercaptoethane sulfonate may include stabilization of the active monomer form, and ability to be delivered directly to the airway and lungs. Encapsulated formulations of sodium 2-mercaptoethane sulfonate may be delivered directly to the respiratory tract, thus having limited systemic exposure from absorption through the lung and reduced risk of systemic side effects.

Particle Properties

In some embodiments, the compositions may be formulated in particles of sizes appropriate to deposit in the upper and lower airways when inhaled.

The microspheres, liposomes, engineered spray-dried particles, and nanoparticles of the invention may be evaluated based on bulk density. Where density of a single solid object, or fluid, is the mass divided by the volume, bulk density is the mass divided by the volume of many particles. The bulk density of a substance may be variable depending on the size of individual particles in the sample. Through micronization, spray-drying, or other processes that affect particle size of the present compositions, the bulk density of a sample may change without going through a chemical transformation. The distance through the respiratory tract that a sample may travel depends in part on bulk density. The bulk density of the present invention may vary between 0.1 g/mL and 5 g/mL, e.g., between 0.1 g/mL and 0.6 g/mL, 0.2 g/mL and 0.7 g/mL, 0.3 g/mL and 0.8 g/mL, 0.4 g/mL and 0.9 g/mL, 0.5 g/mL and 1 g/mL, 1 g/mL and 1.5 g/mL, 1.5 g/mL and 2 g/mL, 2 g/mL and 3 g/mL, 3 g/mL and 4 g/mL, or 4 g/mL and 5 g/mL.

The microspheres, liposomes, engineered spray-dried particles, and nanoparticles used may also be evaluated using the mass median aerodynamic diameter (MMAD). Particles of smaller mass median aerodynamic diameter may travel further into the airways of a subject. Particles with sufficiently small aerodynamic diameters may permeate the lower respiratory tract. Particles with larger mass median aerodynamic diameters may settle into the upper respiratory tract. The present invention contemplates the use of a range of MMAD for targeted delivery to any portion of the respiratory tract necessary. In some embodiments, the MMAD for the particles of the invention may be between 0.1 μm and 10 μm, e.g., between 0.1 μm and 0.2 μm, 0.2 μm and 0.3 μm, 0.3 μm and 0.4 μm, 0.4 μm and 0.5 μm, 0.5 μm and 0.6 μm, 0.6 μm and 0.7 μm, 0.7 μm and 0.8 μm, 0.8 μm and 0.9 μm, 0.9 μm and 1 μm, 1 μm and 1.25 μm, 1.25 μm and 1.5 μm, 1.5 μm and 1.75 μm, 1.75 μm and 2 μm, 2 μm and 2.25 μm, 2.25 μm and 2.5 μm, 2.5 μm and 2.75 μm, 2.75 μm and 3 μm, 3 μm and 3.5 μm, 3.5 μm and 4 μm, 4 μm and 4.5 μm, 4.5 μm and 5 μm, 5 μm and 5.5 μm, 5.5 μm and 6 μm, 6 μm and 6.5 μm, 6.5 μm and 7 μm, 7 μm and 7.5 μm, 7.5 μm and 8 μm, 8 μm and 8.5 μm, 8.5 μm and 9 μm, 9 μm and 9.5 μm, 9.5 μm and 10 μm, 0.1 μm and 1 μm, 1 μm and 3 μm, 3 μm and 5 μm, 5 μm and 7 μm, or 7 μm and 10 μm.

Mass median aerodynamic diameter is the apparent aerodynamic particle size (i.e., the particle size of a water droplet falling at the same terminal velocity as the particle of sample being measured. The Mass median aerodynamic diameter (of a population) equals geometric particle size (of a population) times square root of the bulk density.

In some embodiments, the mass median aerodynamic diameter of the particle may be 3.0 μm-4.5 μm.

In some embodiments, the particle distribution of various geometric sizes may be as follows: 10% of particles<1.2 μm, 50% of particles between 3 μm-4.5 μm, and 40% of particles between 4.0 μm-7.9 μm.

The microsphere, liposome, engineered spray-dried particle, freeze dried particles and nanoparticle compositions used may be evaluated using the fine particle fraction (FPF). FPF is the fraction of particles in a composition that have a mass median aerodynamic diameter equal to or below the desired a mass median aerodynamic diameter for targeted drug delivery, e.g., 2 μm, 3 μm, 4 μm, 5 μm, 6 μm, or 7 μm. The desired aerodynamic diameter may vary according to the target location in the respiratory tract. When the method employed targets the upper respiratory tract, the desired aerodynamic diameter may be larger, whereas when the method employed targets the lower respiratory tract, the desired mass median aerodynamic diameter may be smaller instead. Acceptable ranges of FPF in a composition may be between 10% and 90% of the composition, e.g., between 10% and 20%, 20% and 30%, 30% and 40%, 40% and 50%, 50% and 60%, 60% and 70%, 70% and 80%, 80% and 90%, 10% and 40%, 20% and 50%, 30% and 60%, 40% and 70%, 50% and 80%, 60% and 90%, or 70% and 90% of the composition.

The mass in the FPF that is delivered to a subject is the fine particle dose (FPD), wherein the FPD is the percent of particles with a diameter under 5 μm. Acceptable range of FPD in the methods described herein may be between 0.1 mg and 600 mg, e.g., between 0.1 mg and 1 mg, 0.1 mg and 250 mg, 1 mg and 2 mg, 2 mg and 3 mg, 3 mg and 4 mg, 4 mg and 5 mg, 5 mg and 6 mg, 5 mg to 50 mg, 5 mg to 100 mg, 6 mg and 7 mg, 7 mg and 8 mg, 8 mg and 9 mg, 9 mg and 10 mg, 1 mg and 7 mg, 3 mg and 6 mg, 1 mg and 10 mg, 10 mg and 20 mg, 20 mg and 30 mg, 30 mg and 40 mg, 40 mg and 50 mg, 50 mg to 100 mg, 100 mg to 150 mg, 100 mg to 300 mg, 100 mg to 400 mg, 100 mg to 500 mg, 150 mg to 200 mg, 200 mg to 250 mg, 200 mg to 400 mg, 200 mg to 500 mg, 250 mg to 300 mg, 300 mg to 350 mg, 350 mg to 400 mg, 400 mg to 450 mg, 400 mg to 500 mg, 400 mg to 600 mg, 450 mg to 500 mg, 500 mg to 550 mg, 500 mg to 600 mg, or 550 mg to 600 mg.

The microspheres, liposomes, engineered spray-dried particles, and nanoparticles used may also be evaluated using the mass median aerodynamic diameter (MMAD). Particles of smaller mass median aerodynamic diameter may travel further into the airways of a subject. Particles with sufficiently small aerodynamic diameters may permeate the lower respiratory tract. Particles with larger mass median aerodynamic diameters may settle into the upper respiratory tract. The present invention contemplates the use of a range of MMAD for targeted delivery to any portion of the respiratory tract necessary. In some embodiments, the MMAD for the particles of the invention may be between 0.1 μm and 10 μm, e.g., between 0.1 μm and 0.2 μm, 0.2 μm and 0.3 μm, 0.3 μm and 0.4 μm, 0.4 μm and 0.5 μm, 0.5 μm and 0.6 μm, 0.6 μm and 0.7 μm, 0.7 μm and 0.8 μm, 0.8 μm and 0.9 μm, 0.9 μm and 1 μm, 1 μm and 1.25 μm, 1.25 μm and 1.5 μm, 1.5 μm and 1.75 μm, 1.75 μm and 2 μm, 2 μm and 2.25 μm, 2.25 μm and 2.5 μm, 2.5 μm and 2.75 μm, 2.75 μm and 3 μm, 3 μm and 3.5 μm, 3.5 μm and 4 μm, 4 μm and 4.5 μm, 4.5 μm and 5 μm, 5 μm and 5.5 μm, 5.5 μm and 6 μm, 6 μm and 6.5 μm, 6.5 μm and 7 μm, 7 μm and 7.5, 7.5 μm and 8 μm, 8 μm and 8.5 μm, 8.5 μm and 9 μm, 9 μm and 9.5 μm, 9.5 μm and 10 μm, 0.1 μm and 1 μm, 1 and 3 μm, 3 and 5 μm, 5 and 7 μm, or 7 μm and 10 μm.

Mass median aerodynamic diameter is the apparent aerodynamic particle size (i.e., the particle size of a water droplet falling at the same terminal velocity as the particle of sample being measured. The mass median aerodynamic diameter (of a population) equals geometric particle size (of a population) times square root of the bulk density.

In some embodiments, the mass median aerodynamic diameter of the particle is 3.0 μm-5.5 μm.

In a preferred embodiment, the particle distribution of various geometric sizes are as follows: 10% of particles e<1.2 μm, 50% of particles between 3-4.5 μm, and 40% of particles between 4.0-10 μm.

The microsphere, liposome, engineered spray-dried particle, freeze dried particles and nanoparticle compositions used may be evaluated using the fine particle fraction (FPF). FPF is the fraction of particles in a composition that have a mass median aerodynamic diameter equal to or below the desired a mass median aerodynamic diameter for targeted drug delivery, e.g., 2 μm, 3 μm, 4 μm, 5 μm, 6 μm, or 7 μm. The desired aerodynamic diameter may vary according to the target location in the respiratory tract. When the method employed targets the upper respiratory tract the desired aerodynamic diameter may be larger, whereas when the method employed targets the lower respiratory tract the desired a mass median aerodynamic diameter may be smaller. Acceptable ranges of FPF in a composition are between 10% and 90% of the composition, e.g., between 10% and 20%, 20% and 30%, 30% and 40%, 40% and 50%, 50% and 60%, 60% and 70%, 70% and 80%, 80% and 90%, 10% and 40%, 20% and 50%, 30% and 60%, 40% and 70%, 50% and 80%, 60% and 90% or 70% and 90% of the composition.

Disulfide Bond Reduction

The present invention may provide methods of reducing extracellular disulfide bonds in a viral protein, the method comprising the step of contacting the viral protein with the present compositions.

A reduced level is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%.

Storage and Stability

In some embodiments, the present compositions may be stored in a dry powder form (such as capsule, mono, or multiple dose dry powder inhaler) or in a liquid form (such as ampoules for a nebulizer). In some embodiments, the dry powder form will be reconstituted as solution prior to administration.

In some embodiments, the present compositions may be formulated for stability and resistance to oxidation or other kinds of molecular disintegration. Therefore, and without being bound to theory, more of the drug may reach the site of action in its active, reduced monomeric form. The reach and stabilized activity together may make the product more efficacious, for example at reduced doses.

In some embodiments, the present compositions may be stored at room temperature. In some embodiments, the present compositions may be refrigerated, e.g., at 40° F. In some embodiments, the present compositions may be stored at temperatures below freezing.

Combination Therapies

The present invention may be directed to both single anti-viral treatments, as well as combination therapies. As such, in some embodiments, the present invention may include a combination therapy for the reduction of risk of a viral infection in a subject at risk or the treatment of a viral infection of a subject.

In some embodiments, the present compositions may further include anti-inflammatory, corticosteroid, short-acting beta-agonist, long-acting beta-agonist, short-acting muscarinic antagonist, long-acting muscarinic antagonist, immunosuppressant, antibiotic, antifungal, antihistamine, bronchodilator, anti-infective agent, additional anti-viral agent, or any combination thereof.

In some embodiments, the additional antiviral may be a reverse-transcriptase inhibitor (e.g., remdesivir, abacavir, adefovir, delavirdine, descovy, didanosine, doravirine, efavirenz, emtricitabine, entecavir, etravirine, lamivudine, loviride, nevirapine, rilpivirine, stavudine, tenofovir alafenamide, tenofovir disoproxil, zalcitabine, or zidovudine), RNA or DNA polymerase inhibitor (e.g., acyclovir, cidofovir, penciclovir, famciclovir, foscarnet, ganciclovir, valganciclovir, idoxuridine, ribavirin, taribavirin, sofosbuvir, telbivudine, trifluridine, valaciclovir, or vidarabine), protease inhibitor (e.g., boceprevir, atazanavir, darunavir, fosamprenavir, indinavir, lopinavir, nelfinavir, ritonavir, saquinavir, simeprevir, telaprevir, or tipranavir), integrase inhibitor (e.g., bictegravir, elvitegravir, dolutegravir, or raltegravir), neuraminidase inhibitor (e.g., oseltamivir, zanamivir, laninamivir, or peramivir), ledipasvir, amprenavir, amantadine, umifenovir, baloxavir marboxil, daclatasvir, docosanol, edoxudine, enfuvirtide, fomivirsen, ibacitabine, ibalizumab, letermovir, maraviroc, metisazone, moroxydine, nexavir, nitazoxanide, pleconaril, rimantadine, tromantadine, or vicriviroc.

In some embodiments, the present compositions may include an anti-infective agent. In some embodiments, an anti-infective agent may include quinolones (such as Nalidixic Acid, Cinoxacin, Ciprofloxacin and Norfloxacin and the like), sulfonamides (e.g., Sulfanilamide, Sulfadiazine, Sulfamethoxazole, Sulfisoxazole, Sulfacetamide, and the like), aminoglycosides (e.g., Streptomycin, Gentamicin, Tobramycin, Amikacin, Netilmicin, Kanamycin, and the like), tetracyclines (such as Chlortetracycline, Oxytetracycline, Methacycline, Doxycycline, Minocycline and the like), para-aminobenzoic acid, diaminopyrimidines (such as Trimethoprim, often used in conjunction with Sulfamethoxazole, pyrazinamide, and the like), penicillins (such as Penicillin G, Penicillin V, Ampicillin, Amoxicillin, Bacampicillin, Carbenicillin, Carbenicillin indanyl, Ticarcillin, Azlocillin, Mezlocillin, Piperacillin, and the like), penicillinase resistant penicillin (such as Methicillin, Oxacillin, Cloxacillin, Dicloxacillin, Nafcillin and the like), first generation cephalosporins (such as Cefadroxil, Cephalexin, Cephradine, Cephalothin, Cephapirin, Cefazolin, and the like), second generation cephalosporins (such as Cefaclor, Cefamandole, Cefonicid, Cefoxitin, Cefotetan, Cefuroxime, Aefuroxime axetil, Cefinetazole, Cefprozil, Loracarbef, Ceforanide, and the like), third generation cephalosporins (such as Cefepime, CefoperaZone, Cefotaxime, Ceftizoxime, Ceftriaxone, Ceftazidime, Cefixime, Cefpodoxime, Ceftibuten, and the like), other beta-lactams (such as Imipenem, Meropenem, Aztreonam, Clavulanic acid, Sulbactam, Tazobactam, and the like), beta-lactamase inhibitors (such as Clavulanic acid), Chloramphenicol, macrolides (such as Erythromycin, Azithromycin, Clarithromycin, and the like), Lincomycin, Clindamycin, Spectinomycin, Polymyxin B, polymixins (such as Polymyxin A, B, C or D, E1. Colistin A), or E2, Colistin B or C, and the like) colistin, Vancomycin, Bacitracin, Isoniazid, Rifampin, Ethambutol, Ethionamide, Aminosalicylic Acid, Cycloserine, Capreomycin, sulfones (such as Dapsone, Sulfoxone Sodium, and the like), Clofazimine, Thalidomide, or any other antibacterial agent that can be lipid encapsulated. Anti-infectives may include antifungal agents, which may include polyene antifungals (such as Amphotericin B, Nystatin, Natamycin, and the like), Flucytosine, imidazole (such as Miconazole, Clotrimazole, Econazole, Ketoconazole, and the like), triazoles (such as Itraconazole, Fluconazole, and the like), Griseofulvin, Terconazole, Butoconazole, Ciclopirox, CiclopiroX Olamine, Haloprogin, Tolnaftate, Naftifine, Terbinafine, or any other antifungals that may be lipid encapsulated or complexed and pharmaceutically acceptable salts thereof and combinations thereof.

In some embodiments, the present compositions may include a mucolytic. In some embodiments, the mucolytic may include DNAse, eNaC inhibitors, N-acetylcysteine, L α ureido mercaptopropionic acid, Bromhexine, ascorbic acid, vitamin E, tris(2-carboxyethyl)phosphine hydrochloride, N-butylcysteine, reduced glutathione, N-derivatives and C-derivatives of amino acid cysteine, di-peptide of cysteine and glutamic acid, di-peptide of aspartic acid, or Ambroxol Hydrochloride.

In some embodiments, the present compositions may include a corticosteroid. In some embodiments, the corticosteroid may include any inhalable and/or intranasal steroid. In some embodiments, the corticosteroid may include flunisolide, fluticasone, fluocortolone, triamcinolone, beclomethasone, budesonide, mometasone, ciclesonide, prednisolone, betamethasone, dexamethasone, hydrocortisone, methylprednisolone, or deflazacort.

In some embodiments, the present compositions may include a bronchodilator. In some embodiments, the bronchodilator may include a long-acting bronchodilator such as long-acting β-agonist (LABA), long-acting muscarinic antagonist (LAMA), short-acting bronchodilator such as long-acting β-agonist (SABA), short-acting muscarinic antagonist (SAMA), or any combination thereof. In some embodiments, the bronchodilator may include a beta-2 agonist, such as salbutamol, salmeterol, formoterol and vilanterol anticholinergics, such as ipratropium, tiotropium, aclidinium and glycopyrronium; theophylline; muscarinic antagonist; or methylxanthines.

In some embodiment, the present compositions may include nitric oxide.

In some embodiment, the present compositions may include glycopyrrolate, formoterol fumarate, budesonide, glycopyrronium. fluticasone furoate, vilanterol trifenatate, umeclidinium bromide, or any combination thereof.

In some embodiments, the present compositions may include a drug for treatment of Asthma and COPD. In some embodiments, the present compositions may include aclidinium bromide (Tudorza Pressair), albuterol sulfate inhalation aerosol (Proventil HFA), indacaterol and glycopyrronium inhalation aerosol (Ultibro), bromideinhalation aerosol of budesonide (Pulmicort), mometasone furoate (Nasonex), tiotropium bromide inhalation aerosol (Spiriva), budesonide and formoterol (Symbicort), albuterol sulfate inhalation aerosol (Ventolin HFA), albuterol sulfate inhalation aerosol (ProAir HFA), albuterol sulfate inhalation powder (ProAir Respiclick), albuterol sulfate and ipratropium bromide (Combivent Respimat), albuterol sulfate and ipratropium bromide (Duoneb Inhalation Solution), arformoterol tartrate (Brovana Inhalation Solution), beclomethasone dipropionate inhalation aerosol (QVAR), budesonide inhalation powder (Pulmicort Turbohaler), budesonide inhalation powder (Pulmicort Flexhaler), budesonide and formoterol fumarate (Symbicort Inhalation Aerosol), ciclesonide (Alvesco Inhalation Aerosol), flunisolide (Aerospan HFA), fluticasone furoate and vilanterol trifenatate (Breo Ellipta), fluticasone propionate HFA inhalation aerosol (Flovent HFA), fluticasone propionate inhalation powder (Flovent Diskus), formoterol fumarate inhalation powder (Foradil Aerolizer), formoterol fumarate (Perforomist Inhalation Solution), indacaterol inhalation powder (Arcapta Neohaler), ipratropium bromide HFA inhalation aerosol (Atrovent HFA), levalbuterol sulfate HFA inhalation aerosol (Xopenex), mometasone furoate (Asmanex Inhalation Aerosol HFA), mometasone furoate inhalation powder (Asmanex Twisthaler), mometasone furoate and formoterol fumarate (Dulera Inhalation Aerosol), olodaterol (Striverdi Respimat Inhalation Spray), salmeterol xinafoate powder for inhalation (Serevent Diskus), salmeterol xinafoate/fluticasone propionate powder for inhalation (ADVAIR Diskus), salmeterol xinafoate/fluticasone propionate (ADVAIR HFA), tiotropium bromide (Spiriva Respimat Inhalation Spray), tiotropium bromide inhalation powder (Spiriva Handihaler), umeclidinium inhalation powder (Incruse Ellipta), or umeclidinium and vilanterol inhalation powder (Anoro Ellipta).

In some embodiments, the present compositions may include an immunosuppressant. For the purposes of this disclosure, an "immunosuppressant" is a pharmacological agent designed to inhibit or suppress a body's immune response. Immunosuppressants may be utilized to prevent or treat graft rejection in organ transplantation, manage autoimmune diseases, and/or reduce inflammatory responses. Immunosuppressants may function by targeting various components of an immune system, such as T cells, B cells, cytokines, or specific molecular pathways, thereby mitigating the immune activity that would otherwise lead to tissue damage or graft rejection. The precise mechanism of action may vary depending on the specific immunosuppressant being used. In some embodiments, immunosuppressant may include cyclosporin.

In some embodiments, the present compositions may include an anti-fungal agent. For the purposes of this disclosure, an "anti-fungal" agent is a pharmacological agent designed to inhibit the growth of a fungus. In some embodiments, the anti-fungal agent may include polyene, amphotericin B, nystatin, natamycin, flucytosine, imidazole, miconazole, clotrimazole, econazole, ketoconazole, triazole, itraconazole, fluconazole, griseofulvin, terconazole, butoconazole, ciclopirox, ciclopirox olamine, haloprogin, tolnaftate, naftifine, or terbinafine.

In some embodiments, the present compositions may include a short-acting beta-agonist. For the purposes of this disclosure, a "short-acting beta-agonist" is a pharmacological compound that functions as a bronchodilator to relax lung muscles widen airways by selectively stimulating beta-adrenergic receptors, particularly the beta-2 receptors, located in the bronchial smooth muscle. Upon activation, these receptors may induce muscle relaxation, leading to rapid dilation of the bronchial passages. Short-acting beta-agonists are characterized by their fast onset of action, typically within minutes, and their short duration of effect, generally lasting 4 to 6 hours. These agents are primarily utilized for the acute relief of bronchospasm in conditions such as asthma and COPD. In some embodiments, the short-acting beta-agonist may include bitolterol, fenoterol, isoprenaline, levosalbutamol, orciprenaline, pirbuterol, procaterol, ritodrine, salbutamol, terbutaline, or albuterol.

In some embodiments, the present compositions include a long-acting beta-agonist. For the purposes of this disclosure, a "long-acting beta-agonist" is a pharmacological compound that acts as a bronchodilator to relax lung muscles widen airways by selectively activating beta-2 adrenergic receptors in the bronchial smooth muscle. This activation results in muscle relaxation and prolonged dilation of the bronchial passages. Long-acting beta-agonists are distinguished by their extended duration of action, typically lasting 12 hours or more, making them suitable for the maintenance treatment of respiratory conditions such as asthma and COPD. They provide sustained symptom control and reduce the frequency of exacerbations. In some embodiments, the long-acting beta-agonist may include formoterol, bambuterol, clenbuterol, formoterol, salmeterol, indacaterol, olodaterol, or vilanterol.

In some embodiments, the present compositions include a short-acting muscarinic antagonist. For the purposes of this disclosure, a "short-acting muscarinic antagonist" is a pharmacological compound that exerts its therapeutic effects by competitively inhibiting muscarinic acetylcholine receptors in the bronchial smooth muscle. This inhibition prevents acetylcholine from binding to these receptors, thereby reducing bronchoconstriction and facilitating bronchodilation. Short-acting muscarinic antagonists have a rapid onset of action and a relatively short duration, typically providing relief for up to 4 to 6 hours. They are primarily used for the acute management of bronchospasm in conditions such as COPD. In some embodiments, the short-acting antagonist may include ipratropium.

In some embodiments, the present compositions include a long-acting muscarinic antagonist. For the purposes of this disclosure, a "long-acting muscarinic antagonist" is a pharmacological compound that exerts bronchodilatory effects by selectively inhibiting muscarinic acetylcholine receptors, particularly M3 receptors, in the bronchial smooth muscle. This inhibition prevents acetylcholine-induced bronchoconstriction, resulting in prolonged bronchodilation. Long-acting muscarinic antagonists are characterized by their extended duration of action, typically lasting 12 hours or more, making them suitable for the maintenance treatment of COPD and other respiratory conditions. They provide sustained symptom control and reduce the frequency of exacerbations. In some embodiments, the long-acting muscarinic antagonist may include aclidinium, glycopyrronium, glycopyrrolate, tiotropium, or umeclidinium.

EXAMPLES

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

Example 1: Assessment of Sodium 2-Mercaptoethane Sulfonate on Binding of Virus Spile Protein Receptor Binding Domain with ACE2 Receptor of Human Cell COVID-19 Spike-ACE2 Binding Assay Kit (CODE: CoV-ACE2S2-1) from RayBiotech was used to determinate percentage (%) of binding between SARS-CoV-2 Receptor Binding Domain (RBD) and Angiotensin Converting Enzyme 2 (ACE2). First, 100 μL of sodium 2-mercaptoethane sulfonate and a composition including an encapsulated sodium 2-mercaptoethane sulfonate in a formulation with excipients 1,2-distearoyl-sn-glycero-3-phosphocholine (DSPC) and calcium chloride at concentrations ranging from 0 to 20 mM diluted in 0.9% sodium chloride solution (saline) and ddH2O respectively were incubated in appropriated wells for 1.5 hours at 37° C. under gentle shake. Steps following the incubation were performed as directed in RayBiotech kit's protocol. Briefly, once the incubation was over; wells were washed then incubated in HRP-conjugated IgG antibody solution. After the incubation, wells were washed again. Then, they were incubated in TMB One-Step Substrate Reagent. Lastly, Stop Solution was added to each well. The absorbance (A) was read at 450 nm on a spectrophotometer.

Blanks used $ddH_2O$ for the composition. Negative control contained Assay Diluent from the kit and no RBD. Positive control contained assay reagent and 0 mM set as 100 percent binding (% of binding was calculated with the following equation: ((A of test reagent with test concentration of the composition−A of test reagent with no drug (blank))/(A of positive control−A of blank))×100.

An 85% loading of API was used for testing the COVID-19 spike protein binding.

FIG. 2 shows the percent of SARS-COV-2 spike protein binding with ACE receptor while being treated with increasing concentration of the composition and control.

TABLE 1

| Concentration of Composition (mM) | % Of Binding Composition | Control (+ve) | Control (−ve) | STD (Standard Deviation) |
|---|---|---|---|---|
| 0 | 100 | 100 | 0.2 | 0 |
| 0.625 | 64.5 | 99.0 | 0.2 | 1.6 |
| 1.25 | 57.8 | 99.0 | 0.2 | 1.5 |
| 2.5 | 43.6 | 99.0 | 0.2 | 1.7 |
| 5 | 31.9 | 99.0 | 0.2 | 1.0 |
| 10 | 20.7 | 99.0 | 0.2 | 1.5 |
| 20 | 5.7 | 99.0 | 0.2 | 1.0 |

Table 2 shows the stability of one embodiment of the present invention.

TABLE 2

Stability of Therapeutic Activity MMAD of Composition @ T0, T1, (7-day 40° C. and 75% RH) T2 (6 months storage)

| | 85% API Loading | | | 49% API Loading | | |
|---|---|---|---|---|---|---|
| @ | T0 | T1 | T2 | T0 | T1 | T2 |
| MMAD (μm) | 5.2 | 5.1 | 5.2 | 4.5 | 4.9 | 5.5 |
| % Recovery of Activity | 98 | 92 | 94 | 97 | 93 | 94 |

Table 3 shows an example of composition and particle size of one embodiment of the present invention.

TABLE 3

Composition and Particle Size

| High & Low API Conc. | Formulations $X_{10}$ | $X_{50}$ (μm) | $X_{90}$ | MMAD |
|---|---|---|---|---|
| Sodium 2-Mercaptoethane Sulfonate, 85.8%, w/w | 1.08 | 3.76 | 7.5 | <5.2 |
| Sodium 2-Mercaptoethane Sulfonate, 49.5%, w/w | 1.07 | 3.43 | 7.1 | <5.5 |

COVID-19 Spike-ACE2 Binding Assay Kit (CODE: CoV-ACE2S2-1) from RayBiotech was used to determinate percentage (%) of binding between SARS-CoV-2 RBD and ACE2. The Inhibitory concentration reducing binding by 50% (IC50) was 1.8 mM for the composition. For comparison, for sodium 2-mercaptoethane sulfonate intravenous solution, the IC50 was 2.7 mM.

The result of the experiment demonstrates that the present invention inhibits the binding of SARS-COVID spike protein with human ACE2 receptors in a dose-dependent manner.

Example 2: Assessment of Binding Between Human ACE2 Receptor and SARS-COV-2 Spike Protein when Incubated with Increasing Concentrations of Different Drug Candidates COVID-19 Spike-ACE2 Binding Assay Kit (CODE: CoV-ACE2S2-1) from RayBiotech was used to determinate percentage (%) of binding between SARS-CoV-2 RBD and ACE2.

First, encapsulated sodium 2-mercaptoethane sulfonate (MESNA), unencapsulated sodium 2-mercaptoethane sulfonate, 2-mercaptoethylamine, and N-acetylcysteine were resuspended in ddH2O at 60 mM. A sample of encapsulated sodium 2-mercaptoethane sulfonate at 60 mM was sonicated for 60 seconds (CIL-05B-S). 60 mM solutions were then diluted to 20 mM. A serial dilution by a factor of 2 was used to obtain following concentrations: 10 mM, 5 mM, 2.5 mM, 1.25 mM, and 0.625 mM. 250 μL was pipetted from the first solution tube (20 mM) into the second serial dilution tube (10 mM) and the final volume was filled to 500 μL. This step was repeated for each serial dilution, using 250 μL of the prior concentration until the final concentration was reached.

Next, 100 μL each of encapsulated dry-powder sodium 2-mercaptoethane sulfonate, a solution of encapsulated dry-powder sodium 2-mercaptoethane sulfonate, unencapsulated sodium 2-mercaptoethane sulfonate IV, 2-mercaptoethylamine, and N-acetylcysteine (NAC) at concentrations ranging from 0 to 20 mM were incubated in appropriated wells for 1.5 hours at 37° C. under gentle shake.

Steps following the incubation were performed as directed in RayBiotech kit's protocol. Briefly, once the incubation was over; wells were washed then incubated in HRP-conjugated IgG antibody solution. After the incubation, wells were washed again. Then, the wells were incubated in TMB One-Step Substrate Reagent. Lastly, Stop Solution was added to each well. The absorbance (A) was read at 450 nm on a spectrophotometer.

The blank was $ddH_2O$. Negative control contains Assay Diluent from the kit and no RBD. Wells containing 0 mM of drug was set as 100 percent binding (positive control). The percent of binding was calculated with the following equation: ((A of Test Reagent−A of Blank)/(A of positive control−A of blank))×100.

Figure 3:
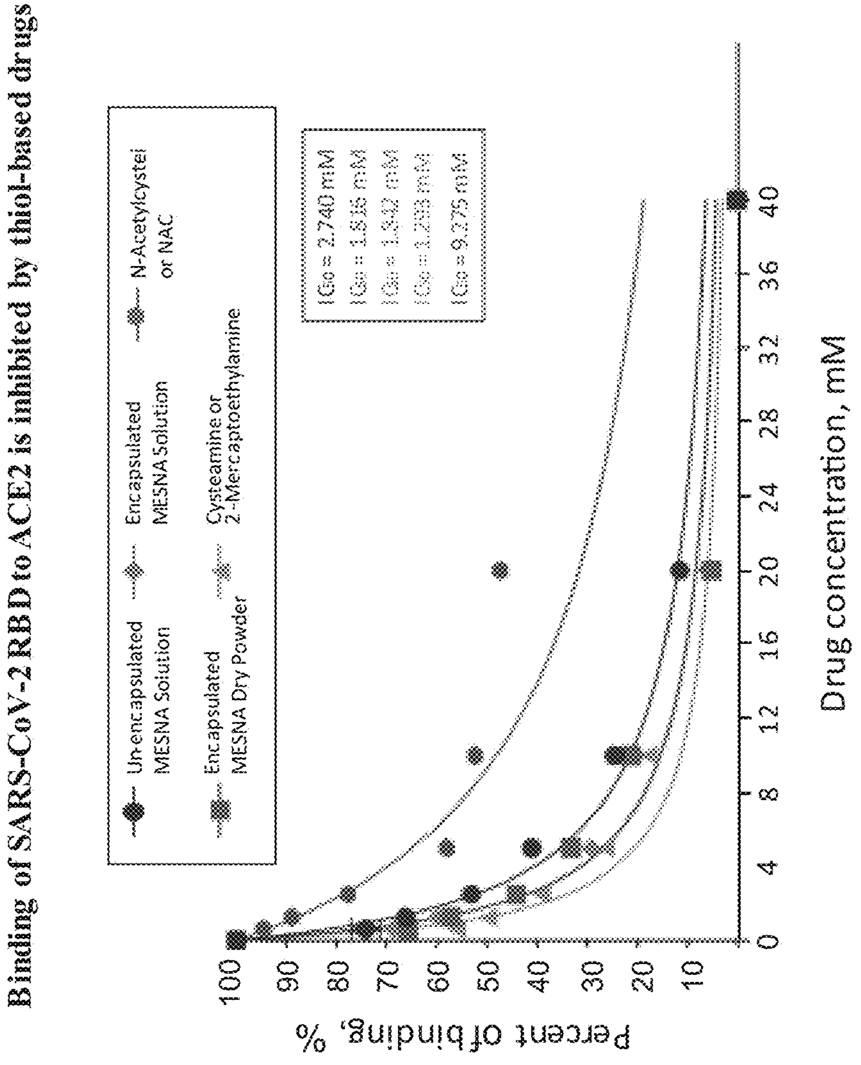
FIG. 3 shows the percentage of ACE2 receptor binding with SARS-COV-2 spike protein when incubated with increasing concentrations of encapsulated sodium 2-mercaptoethane sulfonate, unencapsulated sodium 2-mercaptoethane sulfonate, 2-mercaptoethylamine, and N-acetylcysteine.

Referring now to FIG. 3, FIG. 3 shows the percentage of ACE2 receptor binding with SARS-COV-2 spike protein when incubated with increasing concentrations of encapsulated sodium 2-mercaptoethane sulfonate, unencapsulated sodium 2-mercaptoethane sulfonate, 2-mercaptoethylamine, and N-acetylcysteine.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention. Various modifications and variations of the described disclosure will be apparent to those skilled in the art without departing from the scope and spirit of the disclosure. Although the disclosure has been described in connection with specific embodiments, it should be understood that the disclosure as claimed should not be unduly limited to such specific embodiments. Indeed, various modifications of the described modes for carrying out the disclosure that are obvious to those skilled in the art are intended to be within the scope of the disclosure.

What is claimed is:

1. A method of reducing risk of and treating a viral infection in a subject, the method comprising administering a composition to a subject through inhalation or intranasal route, the composition comprising a plurality of dry-powder inhalable microsphere particles encapsulating sodium 2-mercaptoethane sulfonate in a stabilized active monomeric state, wherein the plurality of dry-powder inhalable microsphere particles are prepared by dissolving sodium 2-mercaptoethane sulfonate in a solvent, forming an oil-in-water emulsion, and evaporating the solvent via spray drying to form the plurality of dry-powder microsphere particles, whereby sodium 2-mercaptoethane sulfonate is stabilized in its active monomeric state, wherein the free thiol group and the terminal charged sulfonate group of sodium 2-mercaptoethane sulfonate in the stabilized active monomeric state are delivered directly to the respiratory tract to synergistically break hydrogen and ionic bonds along with disulfide linkages of viral proteins responsible for binding with host cell receptors and, thereby rendering the viral proteins unrecognizable by the host cell receptors, causing blocking virus entry into the host cell, and protecting the host cell from viral infection, and wherein the viral infection is caused by a coronavirus.

2. The method of claim 1, wherein the coronavirus is severe acute respiratory syndrome coronavirus 2 (SARS-COV-2).

3. The method of claim 2, wherein the SARS-COV-2 is a SARS-COV-2 variant or new mutation, and wherein the SARS-COV-2 variant is Omicron (B.1.1.529), Delta (B.1.617.2), Alpha (B.1.1.7), Gamma (P.1), or Beta (B.1.351) or any new variant.

4. The method of claim 1, wherein the subject is diagnosed with at least one medical condition, wherein the at least one medical condition increases a risk of severe illness from the viral infection and wherein the at least one medical condition is selected from the group consisting of lung disease, sinus disease, airway disease, ear disease, heart disease, high blood pressure, diabetes, kidney disease, liver disease, an immunocompromised state, cancer, obesity, primary ciliary dyskinesia, cystic fibrosis, sinusitis, rhinosinusitis, bronchiolitis obliterans, plastic bronchitis, emphysema, influenza, avian influenza, bronchitis, bronchiectasis, pneumonitis, pneumonia, bronchopulmonary dysplasia (BPD), chronic obstructive pulmonary disease (COPD), chronic obstructive airway disease (COAD), acute respiratory distress syndrome (ARDS), chronic respiratory diseases (CRDS), and COVID-19.

5. The method of claim 1, wherein the composition delivered to the subject is between 0.1 and 120 mg.

6. The method of claim 1, wherein the composition comprises between 20% and 95% by weight of sodium 2-mercaptoethane sulfonate.

7. The method of claim 1, wherein the composition is reconstituted as a solution prior to administration via nebulization or intranasal spray.

8. The method of claim 1, wherein the composition is administered to the subject in combination with at least one pharmacological agent selected from the group consisting of anti-inflammatory, corticosteroid, antihistamine, bronchodilator, beta-2 agonist, short-acting beta-agonist, long-acting beta-agonist, anticholinergic agent, short-acting muscarinic antagonist, long-acting muscarinic antagonist, immunosuppressant, antibiotic, antiviral, antifungal, methylxanthine, and anti-infective agent.

9. The method of claim 1, wherein:

the plurality of dry-powder inhalable microsphere particles have a mass median aerodynamic diameter (MMAD) ranging from 1.0 micron to 5.0 microns; and the plurality of dry-powder inhalable microsphere particles are optimized for deep penetration and lung deposition at a target location of a lung.

10. The method of claim 1, wherein a bulk density of the composition is between 0.1 g/mL and 0.95 g/mL.

11. The method of claim 1, wherein the composition further comprises ascorbic acid.

12. The method of claim 1, wherein the composition further comprises mannitol, calcium chloride, magnesium stearate, edetate disodium (EDTA), sodium acetate, dipalmitoylphosphatidylcholine (DPPC), soy lecithin, egg lecithin, hydrogenated soybean phosphatidylcholine (HSPC), cholesterol, PEG (polyethylene glycol), distearoyl-sn-glycero-phosphoethanolamine (DSPE), distearoylphosphatidylcholine (DSPC), dioleoylphosphatidylcholine (DOPC), egg phosphatidylcholine (EPC), DOPS (dioleoylphosphatidylserine), palmitoyloleoylphosphatidylcholine (POPC), sphingomyelin (SM), methoxy polyethylene glycol (MPEG), dimyristoyl phosphatidylcholine (DMPC), dimyristoyl phosphatidylglycerol (DMPG); distearoylphosphatidylglycerol (DSPG), dierucoylphosphatidylcholine (DEPC), dioleoly-sn-glycero-phophoethanolamine (DOPE), triolein, 1,2-distearoyl-sn-glycero-3-phosphoethanolamine sodium salt (MPEG-DSPE), and 1,2-Dipalmitoyl-sn-glycero-3-phosphorylglycerol sodium salt (DPPG).

13. The method of claim 1, wherein the composition is administered one to four times per day.

* * * * *

SEQUENCE LISTING

```
Sequence total quantity: 35
SEQ ID NO: 1            moltype = AA  length = 60
FEATURE                 Location/Qualifiers
source                  1..60
                        mol_type = protein
                        organism = Severe acute respiratory syndrome-related
                         coronavirus
SEQUENCE: 1
MFVFLVLLPL VSSQSVNLTT RTQLPPAYTN SFTRGVYYPD KVFRSSVLHS TQDLFLPFFS  60

SEQ ID NO: 2            moltype = AA  length = 60
FEATURE                 Location/Qualifiers
source                  1..60
                        mol_type = protein
                        organism = Severe acute respiratory syndrome-related
                         coronavirus
SEQUENCE: 2
NVTWFHAIHV SGTNGTKRFD NPVLPFNDGV YFASTEKSNI IRGWIFGTTL DSKTQSLLIV  60

SEQ ID NO: 3            moltype = AA  length = 60
FEATURE                 Location/Qualifiers
source                  1..60
                        mol_type = protein
                        organism = Severe acute respiratory syndrome-related
                         coronavirus
SEQUENCE: 3
NNATNVVIKV CEFQFCNDPF LGVYYHKNNK SWMESEFRVY SSANNCTFEY VSQPFLMDLE  60

SEQ ID NO: 4            moltype = AA  length = 60
FEATURE                 Location/Qualifiers
source                  1..60
```

```
                        mol_type = protein
                        organism = Severe acute respiratory syndrome-related
                         coronavirus
SEQUENCE: 4
GKQGNFKNLR EFVFKNIDGY FKIYSKHTPI NLVRDLPQGF SALEPLVDLP IGINITRFQT  60

SEQ ID NO: 5            moltype = AA  length = 60
FEATURE                 Location/Qualifiers
source                  1..60
                        mol_type = protein
                        organism = Severe acute respiratory syndrome-related
                         coronavirus
SEQUENCE: 5
CVADYSVLYN SASFSTFKCY GVSPTKLNDL CFTNVYADSF VIRGDEVRQI APGQTGKIAD  60

SEQ ID NO: 6            moltype = AA  length = 60
FEATURE                 Location/Qualifiers
source                  1..60
                        mol_type = protein
                        organism = Severe acute respiratory syndrome-related
                         coronavirus
SEQUENCE: 6
YNYKLPDDFT GCVIAWNSNN LDSKVGGNYN YLYRLFRSKN LKPFERDIST EIYQAGSTPC  60

SEQ ID NO: 7            moltype = AA  length = 60
FEATURE                 Location/Qualifiers
source                  1..60
                        mol_type = protein
                        organism = Severe acute respiratory syndrome-related
                         coronavirus
SEQUENCE: 7
NGVEGFNCYF PLQSYGFQPT NGVGYQPYRV VVLSFELLHA PATVCGPKKS TNLVKNKCVN  60

SEQ ID NO: 8            moltype = AA  length = 60
FEATURE                 Location/Qualifiers
source                  1..60
                        mol_type = protein
                        organism = Severe acute respiratory syndrome-related
                         coronavirus
SEQUENCE: 8
FNFNGLTGTG VLTESNKKFL PFQQFGRDIA DTTDAVRDPQ TLEILDIPTC SFGGVSVITP  60

SEQ ID NO: 9            moltype = AA  length = 60
FEATURE                 Location/Qualifiers
source                  1..60
                        mol_type = protein
                        organism = Severe acute respiratory syndrome-related
                         coronavirus
SEQUENCE: 9
GTNTSNQVAV LYQDVNCTEV PVAIHADQLT PTWRVYSTGS NVFQTRAGCL IGAEHVNNSY  60

SEQ ID NO: 10           moltype = AA  length = 60
FEATURE                 Location/Qualifiers
source                  1..60
                        mol_type = protein
                        organism = Severe acute respiratory syndrome-related
                         coronavirus
SEQUENCE: 10
ECDIPIGAGI CASYQTQTNS PRRARSVASQ SIIAYTMSLG AENSVAYSNN SIAIPTNFTI  60

SEQ ID NO: 11           moltype = AA  length = 60
FEATURE                 Location/Qualifiers
source                  1..60
                        mol_type = protein
                        organism = Severe acute respiratory syndrome-related
                         coronavirus
SEQUENCE: 11
QMAYRFNGIG VTQNVLYENQ KLIANQFNSA IGKIQDSLSS TASALGKLQD VVNQNAQALN  60

SEQ ID NO: 12           moltype = AA  length = 60
FEATURE                 Location/Qualifiers
source                  1..60
                        mol_type = protein
                        organism = Severe acute respiratory syndrome-related
                         coronavirus
SEQUENCE: 12
TLVKQLSSNF GAISSVLNDI LSRLDKVEAE VQIDRLITGR LQSLQTYVTQ QLIRAAEIRA  60

SEQ ID NO: 13           moltype = AA  length = 60
```

```
FEATURE                Location/Qualifiers
source                 1..60
                       mol_type = protein
                       organism = Severe acute respiratory syndrome-related
                        coronavirus
SEQUENCE: 13
SANLAATKMS ECVLGQSKRV DFCGKGYHLM SFPQSAPHGV VFLHVTYVPA QEKNFTTAPA  60

SEQ ID NO: 14          moltype = AA  length = 60
FEATURE                Location/Qualifiers
source                 1..60
                       mol_type = protein
                       organism = Severe acute respiratory syndrome-related
                        coronavirus
SEQUENCE: 14
ICHDGKAHFP REGVFVSNGT HWFVTQRNFY EPQIITTDNT FVSGNCDVVI GIVNNTVYDP  60

SEQ ID NO: 15          moltype = AA  length = 60
FEATURE                Location/Qualifiers
source                 1..60
                       mol_type = protein
                       organism = Severe acute respiratory syndrome-related
                        coronavirus
SEQUENCE: 15
NGVEGFNCYF PLQSYGFQPT YGVGYQPYRV VVLSFELLHA PATVCGPKKS TNLVKNKCVN  60

SEQ ID NO: 16          moltype = AA  length = 60
FEATURE                Location/Qualifiers
source                 1..60
                       mol_type = protein
                       organism = Severe acute respiratory syndrome-related
                        coronavirus
SEQUENCE: 16
FNFNGLTGTG VLTESNKKFL PFQQFGRDID DTTDAVRDPQ TLEILDIPTC SFGGVSVITP  60

SEQ ID NO: 17          moltype = AA  length = 60
FEATURE                Location/Qualifiers
source                 1..60
                       mol_type = protein
                       organism = Severe acute respiratory syndrome-related
                        coronavirus
SEQUENCE: 17
ECDIPIGAGI CASYQTQTNS HRRARSVASQ SIIAYTMSLG AENSVAYSNN SIAIPINFTI  60

SEQ ID NO: 18          moltype = AA  length = 60
FEATURE                Location/Qualifiers
source                 1..60
                       mol_type = protein
                       organism = Severe acute respiratory syndrome-related
                        coronavirus
SEQUENCE: 18
TLVKQLSSNF GAISSVLNDI LARLDKVEAE VQIDRLITGR LQSLQTYVTQ QLIRAAEIRA  60

SEQ ID NO: 19          moltype = AA  length = 60
FEATURE                Location/Qualifiers
source                 1..60
                       mol_type = protein
                       organism = Severe acute respiratory syndrome-related
                        coronavirus
SEQUENCE: 19
ICHDGKAHFP REGVFVSNGT HWFVTQRNFY EPQIITTHNT FVSGNCDVVI GIVNNTVYDP  60

SEQ ID NO: 20          moltype = AA  length = 60
FEATURE                Location/Qualifiers
source                 1..60
                       mol_type = protein
                       organism = Severe acute respiratory syndrome-related
                        coronavirus
SEQUENCE: 20
NVTWFHAIHV SGTNGTKRFA NPVLPFNDGV YFASTEKSNI IRGWIFGTTL DSKTQSLLIV  60

SEQ ID NO: 21          moltype = AA  length = 60
FEATURE                Location/Qualifiers
source                 1..60
                       mol_type = protein
                       organism = Severe acute respiratory syndrome-related
                        coronavirus
SEQUENCE: 21
GKQGNFKNLR EFVFKNIDGY FKIYSKHTPI NLVRGLPQGF SALEPLVDLP IGINITRFQT  60
```

```
SEQ ID NO: 22          moltype = AA  length = 60
FEATURE                Location/Qualifiers
source                 1..60
                       mol_type = protein
                       organism = Severe acute respiratory syndrome-related
                        coronavirus
SEQUENCE: 22
CVADYSVLYN SASFSTFKCY GVSPTKLNDL CFTNVYADSF VIRGDEVRQI APGQTGNIAD  60

SEQ ID NO: 23          moltype = AA  length = 60
FEATURE                Location/Qualifiers
source                 1..60
                       mol_type = protein
                       organism = Severe acute respiratory syndrome-related
                        coronavirus
SEQUENCE: 23
NGVKGFNCYF PLQSYGFQPT YGVGYQPYRV VVLSFELLHA PATVCGPKKS TNLVKNKCVN  60

SEQ ID NO: 24          moltype = AA  length = 60
FEATURE                Location/Qualifiers
source                 1..60
                       mol_type = protein
                       organism = Severe acute respiratory syndrome-related
                        coronavirus
SEQUENCE: 24
ECDIPIGAGI CASYQTQTNS PRRARSVASQ SIIAYTMSLG VENSVAYSNN SIAIPTNFTI  60

SEQ ID NO: 25          moltype = AA  length = 60
FEATURE                Location/Qualifiers
source                 1..60
                       mol_type = protein
                       organism = Severe acute respiratory syndrome-related
                        coronavirus
SEQUENCE: 25
MFVFLVLLPL VSSQSVNFTN RTQLPSAYTN SFTRGVYYPD KVFRSSVLHS TQDLFLPFFS  60

SEQ ID NO: 26          moltype = AA  length = 60
FEATURE                Location/Qualifiers
source                 1..60
                       mol_type = protein
                       organism = Severe acute respiratory syndrome-related
                        coronavirus
SEQUENCE: 26
NNATNVVIKV CEFQFCNYPF LGVYYHKNNK SWMESEFRVY SSANNCTFEY VSQPFLMDLE  60

SEQ ID NO: 27          moltype = AA  length = 60
FEATURE                Location/Qualifiers
source                 1..60
                       mol_type = protein
                       organism = Severe acute respiratory syndrome-related
                        coronavirus
SEQUENCE: 27
GKQGNFKNLR EFVFKNIDGY FKIYSKHTPI NLVRGLPQGF SALEPLVDLP IGINITRFQT  60

SEQ ID NO: 28          moltype = AA  length = 60
FEATURE                Location/Qualifiers
source                 1..60
                       mol_type = protein
                       organism = Severe acute respiratory syndrome-related
                        coronavirus
SEQUENCE: 28
CVADYSVLYN SASFSTFKCY GVSPTKLNDL CFTNVYADSF VIRGDEVRQI APGQTGTIAD  60

SEQ ID NO: 29          moltype = AA  length = 60
FEATURE                Location/Qualifiers
source                 1..60
                       mol_type = protein
                       organism = Severe acute respiratory syndrome-related
                        coronavirus
SEQUENCE: 29
NGVKGFNCYF PLQSYGFQPT YGVGYQPYRV VVLSFELLHA PATVCGPKKS TNLVKNKCVN  60

SEQ ID NO: 30          moltype = AA  length = 60
FEATURE                Location/Qualifiers
source                 1..60
                       mol_type = protein
                       organism = Severe acute respiratory syndrome-related
                        coronavirus
```

-continued

```
SEQUENCE: 30
GTNTSNQVAV LYQDVNCTEV PVAIHADQLT PTWRVYSTGS NVFQTRAGCL IGAEYVNNSY  60

SEQ ID NO: 31          moltype = AA  length = 60
FEATURE                Location/Qualifiers
source                 1..60
                       mol_type = protein
                       organism = Severe acute respiratory syndrome-related
                        coronavirus
SEQUENCE: 31
SANLAAIKMS ECVLGQSKRV DFCGKGYHLM SFPQSAPHGV VFLHVTYVPA QEKNFTTAPA  60

SEQ ID NO: 32          moltype = AA  length = 60
FEATURE                Location/Qualifiers
source                 1..60
                       mol_type = protein
                       organism = Severe acute respiratory syndrome-related
                        coronavirus
SEQUENCE: 32
MFVFLVLLPL VSSQSVNFRN RTQLPSAYTN SFTRGVYYPD KVFRSSVLHS TQDLFLPFFS  60

SEQ ID NO: 33          moltype = AA  length = 60
FEATURE                Location/Qualifiers
source                 1..60
                       mol_type = protein
                       organism = Severe acute respiratory syndrome-related
                        coronavirus
SEQUENCE: 33
YNYKLPDDFT GCVIAWNSNN LDSKVGGNYN YRYRLFRSKN LKPFERDIST EIYQAGSKPC  60

SEQ ID NO: 34          moltype = AA  length = 60
FEATURE                Location/Qualifiers
source                 1..60
                       mol_type = protein
                       organism = Severe acute respiratory syndrome-related
                        coronavirus
SEQUENCE: 34
ECDIPIGAGI CASYQTQTNS RRRARSVASQ SIIAYTMSLG AENSVAYSNN SIAIPTNFTI  60

SEQ ID NO: 35          moltype = AA  length = 60
FEATURE                Location/Qualifiers
source                 1..60
                       mol_type = protein
                       organism = Severe acute respiratory syndrome-related
                        coronavirus
SEQUENCE: 35
QMAYRFNGIG VTQNVLYENQ KLIANQFNSA IGKIQDSLSS TASALGKLQN VVNQNAQALN  60
```